United States Patent [19]

Lamm et al.

[11] Patent Number: 5,510,468
[45] Date of Patent: Apr. 23, 1996

[54] AMINO BENZOPHENONE DYE

[75] Inventors: Gunther Lamm, Hassloch; Helmut Reichelt, Neustadt; Ortwin Schaffer, Ludwigshafen, all of Germany

[73] Assignee: BASF Aktiengesellschaft, Ludwigshafen, Germany

[21] Appl. No.: 281,035

[22] Filed: Jul. 27, 1994

Related U.S. Application Data

[62] Division of Ser. No. 87,792, filed PCT/EP92/00292, Feb. 10, 1992, Pat. No. 5,380,859.

[30] Foreign Application Priority Data

Feb. 20, 1991 [DE] Germany .................. 41 05 257.9

[51] Int. Cl.$^6$ .................. C09B 29/42; C09B 31/153
[52] U.S. Cl. .................. 534/772; 534/573; 534/583; 534/642; 534/730; 534/757; 534/764; 534/773; 534/782; 534/784; 534/821; 534/827; 534/836; 534/837; 534/845; 534/851; 534/861; 534/869
[58] Field of Search .................. 534/772, 861, 534/869, 642, 730, 757, 573, 764, 583, 784, 785, 782, 773, 821, 827, 836, 837, 845, 851

[56] References Cited

U.S. PATENT DOCUMENTS

| | | | |
|---|---|---|---|
| 3,956,265 | 5/1976 | Leng et al. | 534/772 |
| 4,247,456 | 1/1981 | Von Brachel et al. | 534/772 |
| 4,772,292 | 9/1988 | Hahnke et al. | 534/772 X |
| 5,151,506 | 9/1992 | Bach et al. | 534/772 |
| 5,153,356 | 10/1992 | Lamm et al. | 562/46 |
| 5,380,859 | 1/1995 | Lamm et al. | 546/296 |

FOREIGN PATENT DOCUMENTS

| | | | |
|---|---|---|---|
| 1183529 | 3/1985 | Canada | 534/772 |
| 9360749 | 7/1974 | United Kingdom | 534/772 |

*Primary Examiner*—Floyd D. Higel
*Attorney, Agent, or Firm*—Oblon, Spivak, McClelland, Maier & Neustadt

[57] ABSTRACT

There are described benzophenoneazo dyes of the formula

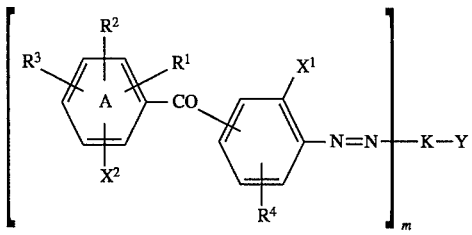

where the ring A can be benzofused and a benzofused ring A can be overbridges, m is 1 or 2, K is the radical of a coupling component, Y is hydrogen or arylazo,
one of the two radicals $X^1$ and $X^2$ is hydrogen and the other is hydroxysulfonyl, $R^1$, $R^2$ and $R^3$ are independently of the others hydrogen, halogen, $C_1$–$C_{12}$-alkyl, cyclohexyl, phenyl, 2-hydroxy-ethylsulfonyl or $C_1$–$C_4$-alkoxy or, when m is 1 and Y is hydrogen, one of these substituents can also be the radical of the formula

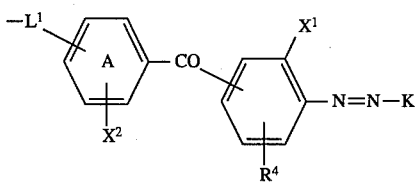

where $L^1$ is a chemical bond or a bridge member, and $X^1$, $X^2$, $R^4$, K and the ring A are each as defined above, and $R^4$ is hydrogen, halogen or $C_1$–$C_4$-alkoxy,
with the proviso that there is at least one water-solublizing group in the molecule, novel pyridone compounds, a process for preparing disulfonated pyridone compounds, and the use of the novel dyes for dyeing natural or synthetic substrates.

24 Claims, No Drawings

AMINO BENZOPHENONE DYE

This application is a divisional of application Ser. No. 08/087,792, filed Jul. 16, 1993, now U.S. Pat. No. 5,380,859, which was filed as International Application No. PCT/EP92/00281 on Feb. 10, 1992.

The present invention relates to a novel benzophenoneazo dye of the formula I

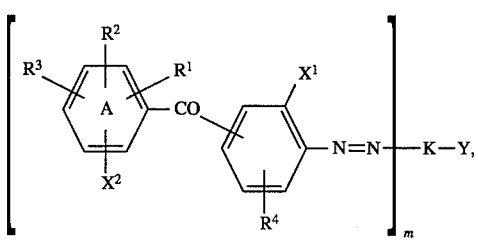

where the ring A can be benzofused and a benzofused ring A can be bridged by $C_2H_4$, m is 1 or 2, K is the radical of a 6-hydroxypyrid-2-one derivative which in ring position 3 is unsubstituted or substituted by carbamoyl, $C_2$–$C_5$-alkanoyl hydroxysulfonylmethyl or hydroxysulfonyl, or is the radical of a coupling component of the phenylazopyridone, diaminopyridine, imidazolopyridine, aminopyrazole, hydroxypyrazole, aminothiazole, pyrimidine, indole, quinolone, aniline or aminonaphthalene series, Y, when m is 1, is hydrogen or the radical —N=N—Q, where Q is the radical of a diazo or coupling component, or, when m is 2, is hydrogen, $X^1$ and $X^2$ are identical or different and each is independently of the other hydrogen or hydroxysulfonyl, $R^1$, $R^2$ and $R^3$ are identical or different and each is independently of the others hydrogen, halogen, $C_1$–$C_{12}$-alkyl, cyclohexyl, phenyl, 2-hydroxyethylsulfonyl or $C_1$–$C_4$-alkoxy or, when m is 1 and Y is hydrogen, one of these substituents can also be the radical of the formula

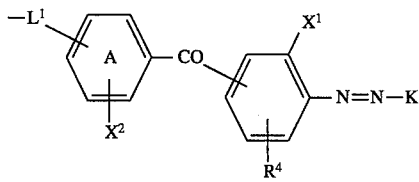

where $L^1$ is a chemical bond, $C_1$–$C_4$-alkylene, oxygen or a radical of the formula O—$CH_2$, O—$CH_2CH_2$—O, O—$CH_2CH_2CH_2$—O or O—$CH(CH_3)CH_2$—O, and $X^1$, $X^2$, $R^4$, K and the ring A are each as defined above, and $R^4$ is hydrogen, halogen or $C_1$–$C_4$-alkoxy, with the proviso that there is at least one water-solubilizing group in the molecule, to novel pyridone compounds, to a process for preparing disulfonated pyridone compounds and to the use of the novel dyes for dyeing natural or synthetic substrates.

The novel benzophenoneazo dyes of the formula I are shown in the form of the free acid. However, their salts are of course also included.

The salts in question are metal or ammonium salts. Metal salts are in particular the lithium, sodium or potassium salts. Ammonium salts suitable for the purposes of the present invention are those salts which have either substituted or unsubstituted ammonium cations. Substituted ammonium cations are for example monoalkyl-, dialkyl-, trialkyl-, tetraalkyl- or benzyltrialkyl-ammonium cations or those cations which are derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl here is to be understood as meaning in general straight-chain or branched $C_1$–$C_{20}$-alkyl, which can be substituted by hydroxyl groups and/or interrupted by oxygen atoms.

EP-A-302,401 and the earlier patent application EP-A-413,229 disclose benzophenoneazo dyes which, however, have no water-solubilizing group in the molecule.

DE-A-2,223,622 describes a dye with 3-amino-benzophenone-4-sulfonic acid as diazo component and 1-methyl-6-hydroxy-3,4-trimethylenepyrid-2-one as coupling component.

Furthermore, DE-A-3,316,887 describes an azo dye whose coupling component is 1-hydroxysulfonylbenzyl-3-hydroxysulfonyl-4-methyl-6-hydroxypyrid-2-one.

It is an object of the present invention to provide novel benzophenoneazo dyes which have at last one water-solubilizing group in the molecule and advantageous application properties.

We have found that this object is achieved by the benzophenoneazo dyes of the formula I defined at the beginning.

Any alkyl or alkylene appearing in the above-mentioned formula I may be either straight-chain or branched.

If substituted phenyl groups appear in the formulae of the dyes of the invention, they generally have from 1 to 3 substituents. Suitable substituents are for example $C_1$–$C_4$-alkyl, $C_1$–$C_4$-alkoxy, halogen and hydroxysulfonyl.

Water-solubilizing groups for the purposes of the present invention are for example hydroxysulfonyl and carboxyl, the former being preferred.

Coupling components KH of the pyridone or phenylazopyridone series conform for example to the formula IIc

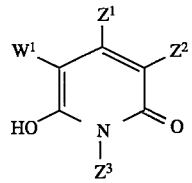

where $W^1$ is hydrogen or a radical of the formula

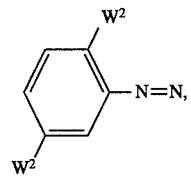

wherein $W^2$ and $W^3$ are identical or different and each is independently of the other hydrogen, methyl, ethyl or methoxy, $Z^1$ is hydrogen, $C_1$–$C_4$-alkyl or phenyl, $Z^2$ is hydrogen, carbamoyl, $C_2$–$C_5$-alkanoyl, hydroxysulfonylmethyl or hydroxysulfonyl, and $Z^3$ is hydrogen or $C_1$–$C_8$-alkyl which may be substituted by phenyl or hydroxysulfoylphenyl and may be interrupted by from 1 to 3 oxygen atoms in ether function.

Coupling components KH of the diaminopyridine series conform for example to the formula IId

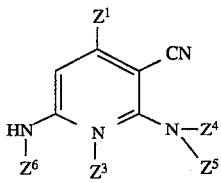 (IId)

where

Z⁴, Z⁵ and Z⁶ are identical or different and each is independently of the other hydrogen, $C_1$–$C_{12}$-alkyl which may be interrupted by from 1 to 4 oxygen atoms in ether function and may be hydroxyl-, phenoxy-, phenyl-, hydroxysulfonylphenyl- or $C_1$–$C_4$-alkanoyloxy-substituted, or hydroxysulfonylphenyl or Z⁶ can also be 3-(1-imidazolyl)propyl and Z⁵ can also be the radical

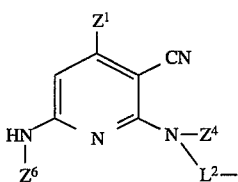

where L² is $C_2$–$C_4$-alkylene and Z¹, Z⁴ and Z⁵ are each as defined above, and Z¹ is as defined above.

Coupling components KH of the imidazolopyridine series conform for example to the formula IIe

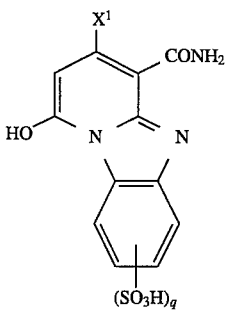 (IIe)

where q is 0 or 1, and Z¹ is as defined above.

Coupling components KH of the aminopyrazole or pyrazolone series conform for example to the formula IIf

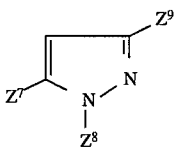 (IIf)

where

Z⁷ is amino or hydroxyl,

Z⁸ is unsubstituted or phenyl- or hydroxysulfonyl-phenyl-substituted $C_1$–$C_4$-alkyl or substituted or unsubstituted phenyl, and Z⁹ is hydrogen, $C_1$–$C_4$-alkyl, carboxyl or $C_1$–$C_4$-alkoxycarbonyl.

Coupling components KH of the aminothiazole series conform for example to the formula IIg

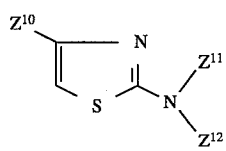 (IIg)

where

Z¹⁰ is $C_1$–$C_4$-alkyl, substituted or unsubstituted phenyl or thienyl, and

Z¹¹ and Z¹² are identical or different and each is independently of the other $C_1$–$C_8$-alkyl which may be interrupted by from 1 to 3 oxygen atoms in other function.

Coupling components KH of the quinoline series conform for example to the formula IIh

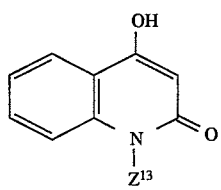 (IIh)

where

Z¹³ is $C_1$–$C_4$-alkyl.

Coupling components KH of the pyrimidine series conform for example to the formula IIi or IIj

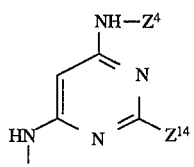 (IIi)

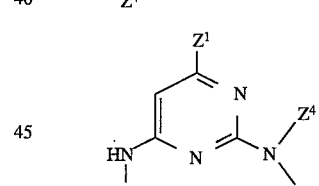 (IIj)

where

Z¹⁴ is $C_1$–$C_4$-alkyl or phenyl, and

Z¹, Z⁴, Z⁵ and Z⁶ are each as defined above.

Coupling components KH of the indols series conform for example to the formula IIk

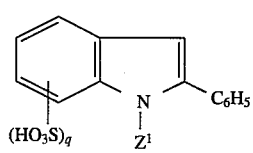 (IIk)

where Z¹ and q are each as defined above.

Coupling components KH of the aniline series conform for example to the formula III

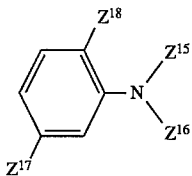

where $Z^{15}$ is hydrogen or $C_1$–$C_8$-alkyl which may be unsubstituted or substituted by hydroxyl, $C_1$–$C_4$-alkoxy, cyano, $C_1$–$C_4$-alkanoyloxy, $C_1$–$C_4$-alkoxycarbonyloxy, $C_1$–$C_4$-alkylaminocarbonyloxy, phenyl, hydroxysulfonylphenyl, $C_1$–$C_4$-alkoxycarbonyl or chlorine-, hydroxyl-, $C_1$–$C_4$-alkoxy- or phenoxy-substituted $C_1$–$C_4$-alkoxycarbonyl, $Z^{16}$ is hydrogen or $C_1$–$C_6$-alkyl which may be substituted by phenyl, hydroxysulfonylphenyl, $C_1$–$C_4$-alkoxy-carbonyl or chlorine-, hydroxyl-, $C_1$–$C_4$-alkoxy- or phenoxy-substituted $C_1$–$C_4$-alkoxycarbonyl, $Z^{17}$ is hydrogen, $C_1$–$C_4$-alkyl, $C_1$–$C_4$-alkoxy, chlorine, bromine or the radical —NH—CO—Q, where Q is $C_1$–$C_4$-alkyl, which may be $C_1$–$C_4$-alkoxy-, phenoxy-, cyano-, hydroxyl-, chlorine- or $C_1$–$C_4$-alkanoyloxy-substituted, or unsubstituted or $C_1$–$C_4$-alkoxy-substituted phenoxy, and $Z^{18}$ is hydrogen, $C_1$–$C_4$-alkyl or $C_1$–$C_4$-alkoxy.

Coupling components KH of the aminonaphthalene series conform for example to the formula IIm

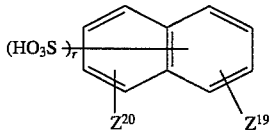

where $Z^{19}$ is amino, phenylamino, $C_1$–$C_4$-alkanoylamino or benzoylamino, $Z^{20}$ is hydrogen or hydroxyl, and r is 1 or 2.

If Y is the radical —N=N—Q, Q is the radical of a diazo or coupling component.

Suitable diazo components $Q^1$—$NH_2$ are derived for example from the aniline series. They conform for example to the formula III

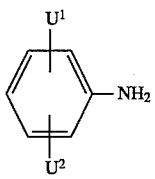

where $U^1$ is hydrogen, $C_1$–$C_4$-alkyl or hydroxysulfonyl and $U^2$ is hydrogen, unsubstituted or sulfato-substituted $C_1$–$C_4$-alkyl, hydroxysulfonyl, phenylsulfonyloxy or 6-methyl-7-hydroxysulfonylbenzothiazol-2-yl.

Suitable coupling components $Q^2$—H are for example the abovementioned compounds of the formulae IIc to IIm, of which coupling components of the formula IId or IIg are particularly noteworthy.

Radicals $R^1$, $R^2$, $R^3$, $Z^1$, $Z^2$, $Z^3$, $Z^4$, $Z^5$, $Z^6$, $Z^8$, $Z^9$, $Z^{10}$, $Z^{11}$, $Z^{12}$, $Z^{13}$, $Z^{14}$, $Z^{15}$, $Z^{16}$, $Z^{17}$, $Z^{18}$, $U^1$ and $U^2$ are each for example methyl, ethyl, propyl, isopropyl, butyl, isobutyl or sec-butyl.

Radicals $R^1$, $R^2$, $R^3$, $Z^3$, $Z^4$, $Z^5$, $Z^6$, $Z^{11}$, $Z^{12}$, and $Z^{15}$ and $Z^{16}$ may each also be for example pentyl, isopentyl, neopentyl, tert-pentyl or hexyl.

Radicals $R^1$, $R^2$, $R^3$, $Z^3$, $Z^4$, $Z^5$, $Z^6$, $Z^{11}$ and $Z^{12}$ may each also be for example heptyl, octyl, 2-ethylhexyl or isooctyl.

Radicals $R^1$, $R^2$, $R^3$, $Z^4$, $Z^5$ and $Z^6$ may each also be for example nonyl, isononyl, decyl, isodecyl, undecyl or dodecyl. (The above designations isooctyl, isononyl and isodecyl are trivial names derived from oxo process alcohols—cf. Ullmanns Enzyklopädie der technischen Chemie, 4th edition, volume 7, pages 215 to 217, and also volume 11, pages 435 and 436.)

Radicals $Z^3$, $Z^4$, $Z^5$, $Z^6$, $Z^8$, $Z^{15}$ and $Z^{16}$ may each also be for example benzyl, hydroxysulfonylbenzyl, 1- or 2-phenylethyl or 1- or 2-(hydroxysulfonylphenyl)ethyl.

Radicals $Z^8$ and $Z^{10}$ may each also be for example phenyl, 2-, 3- or 4-methylphenyl, 2-, 3- or 4-methoxyphenyl, 2-, 3- or 4-chlorophenyl, 2,4-dichlorophenyl, 2-, 3- or 4-bromophenyl or 2-, 3- or 4-hydroxysulfonylphenyl.

Radicals $Z^3$, $Z^4$, $Z^5$, $Z^6$, $Z^{11}$ and $Z^{12}$ may each also be for example 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxa-heptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl or 3,6,9-trioxaundecyl.

Radicals $Z^4$, $Z^5$ and $Z^6$ may each also be for example 2-hydroxyethyl, 2- or 3-hydroxypropyl, 2- or 4-hydroxybutyl, 5-hydroxy-3-oxapentyl, 6-hydroxy-4-oxahexyl, 8-hydroxy-4-oxaoctyl, 9-hydroxy-4,7-dioxanonyl, 2-phenoxyethyl, 2- or 3-phenoxypropyl, 2- or 4-phenoxybutyl, 6-phenoxy-4-oxahexyl, 3,6,9,12-tetraoxatridecyl, 3,6,9,12-tetraoxatetradecyl, 2-formyloxyethyl, 2-acetyloxyethyl, 2- or 3-formyloxypropyl, 2- or 3-acetyloxypropyl, 2- or 4-formyloxybutyl, 2- or 4-acetyloxybutyl, 5-formyloxy-3-oxapentyl, 5-acetyloxy-3-oxapentyl, 6-formyloxy-4-oxaheptyl, 6-acetyloxy-4-oxyheptyl, 8-formyloxy-4-oxaoctyl, 8-acetyloxy-4-oxaoctyl, 9-formyloxy-4,7-dioxanonyl or 9-acetyloxy-4,7-dioxanonyl.

$Z^2$ is for example acetyl, propionyl, butyryl, isobutyryl or pentanoyl.

$Z^9$ may also be for example methoxycarbonyl, ethoxycarbonyl, propoxycarbonyl, isopropoxycarbonyl, butoxycarbonyl or isobutoxycarbonyl.

$R^{15}$ may also be for example 2-hydroxyethyl, 2- or 3-hydroxypropyl, 4-hydroxybutyl, 5-hydroxypentyl, 6-hydroxyhexyl, 2-methoxyethyl, 2-ethoxyethyl, 2-propoxyethyl, 2-butoxyethyl, 2-cyanoethyl, 2-formyloxyethyl, 2-acetyloxyethyl, 2-propionyloxyethyl, 2-butyryloxyethyl, 4-acetyloxybutyl, 2-methoxycarbonyloxyethyl, 2-methylaminocarbonyloxyethyl, 2-ethylaminocarbonyloxyethyl, 2-propylaminocarbonyloxyethyl or 2-butylamiocarbonyloxyethyl.

$Z^{15}$ and $Z^{16}$ may each also be for example 2-methoxycarbonylethyl, 2-ethoxycarbonylethyl, 2-propoxycarbonylethyl, 2-isopropoxycrbonylethyl, 2-butoxycrbonylethyl, 2-isobutoxycarbonylethyl, 2-sec-butoxycarbonylethyl, 2-(2-chloroethoxycarbonyl)ethyl, 2-(2-hydroxyethoxycarbonyl)ethyl, 2-(2-methopxyethoxycarbonyl)ethyl, 2-(2-ethoxyethoxycarbonyl)ethyl, 2-(2-propoxyethoxycarbonyl)ethyl, 2-(2-isopropoxycrbonyl)ethyl, 2-(2-butoxyethoxycarbonyl)ethyl or 2-(2-phenoxyethoxycarbonyl)ethyl, When $Z^{17}$ is the radical NH—CO—Q, Q is for example methyl, ethyl, propyl, isoppropyl, butyl, methoxymethyl, ethoxymethyl, 1- or 2-methoxyethyl, 1- or 2-ethoxyethyl, phenoxymethyl, 1- or 2-phenoxyethyl, cyanomethyl, 2-cyanoethyl, 3-cyanopropyl, 4-cyanobutyl, hydroxymethyl, 1- or 2-hydroxyethyl, 2- or 3-hydroxypropyl, 4-hydroxybutyl, chloromethyl, 2-chloroethyl, formyloxymethyl, acetyloxymethyl, 2-formyloxyethyl, 2-acetyloxyethyl, 2-propionyloxyethyl, 2-butyryloxyethyl, 3-formyloxypropyl, 4-acetyloxybutyl, phenoxy, 2-methoxyphenoxy, 4-methoxyphenoxy, 4-ethoxyphenoxy or 4-isopropoxyphenoxy.

$U^2$ may also be for example 2-sulfatoethyl or 2- or 3-sulfatopropyl.

Radicals $R^1$, $R^2$, $R^3$ and $R^4$ may each also be for example fluorine, chlorine or bromine.

Radicals $R^1$, $R^2$, $R^3$, $Z^{17}$ and $Z^{18}$ may each also be for example methoxy, ethoxy, propoxy, isopropoxy, butoxy, isobutoxy or sec-butoxy.

L is for example methylene, ethylene, 1,2- or 1,3-propylene, isopropylidene or 1,2-, 1,3-, 2,3- or 1,4-butylene.

Preference is given to benzophenoneazo dyes which conform to the formula Ia

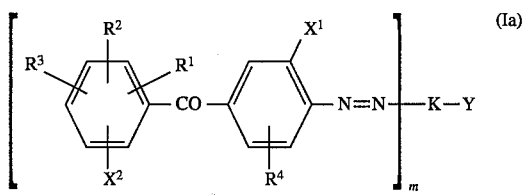

where m, K, Y, $X^1$, $X^2$, $R^1$, $R^2$, $R^3$ and $R^4$ are each as defined above.

Preference is further given to benzophenoneazo dyes of the formula I where one of the two radicals $X^1$ and $X^2$ is hydrogen and the other is hydroxysulfonyl.

Particular preference is given to benzophenoneazo dyes of the formula I where K is the radical of a 6-hydroxypyrid-2-one derivative which in ring position 3 is unsubstituted or substituted by carbamoyl, $C_2-C_5$-alkanoyl, hydroxysulfonylmethyl or hydroxysulfonyl, or is the radical of a coupling component of the diaminopyridine, aminopyrazole, pyrimidine, indole or aminonaphthalene series.

of note are benzophenoneazo dyes of the formula I where K is a radical of the formula IIc, IId, IIf (Z'=amino), IIi, IIj, IIk or IIm.

Also of note are benzophenoneazo dyes of the formula I where m is 1 and Y is hydrogen.

Also of note are benzophenoneazo dyes of the formula I where $R^1$, $R^2$ and $R^3$ are each independently of the other hydrogen, chlorine, $C_1-C_4$-alkyl, in particular methyl or ethyl, methoxy or ethoxy.

Of particular importance are benzophenoneazo dyes which conform to the formula Ib, Ic or Id

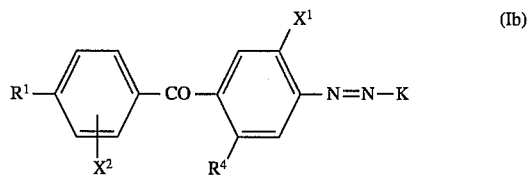

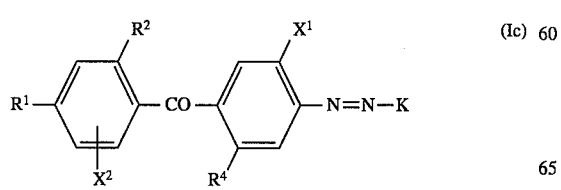

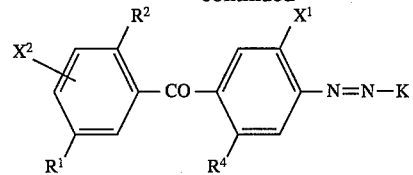

where one of the radicals $X^1$ and $X^2$ is hydrogen and the other is hydroxysulfonyl, $R^1$ and $R^2$ are independently of each other chlorine, $C_1-C_4$-alkyl, in particular methyl or ethyl, methoxy or ethoxy, $R^4$ is hydrogen or methoxy, and K is in each case as defined above.

Also of particular importance are benzophenoneazo dyes of the formula Ic or If

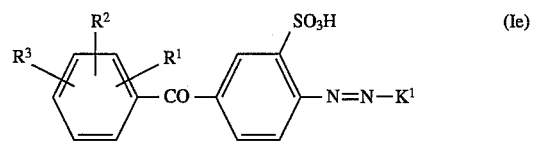

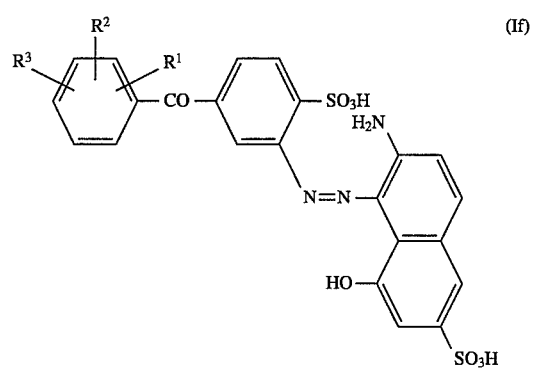

where $R^1$, $R^2$ and $R^3$ are each as defined above and $K^1$ is 1-phenyl-3-methyl-5-aminopyrazol-4-yl, 2-amino-6-hydroxysulfonyl-8-hydroxynaphth-1-yl or a radical of the formula IIn, IIo or IIp

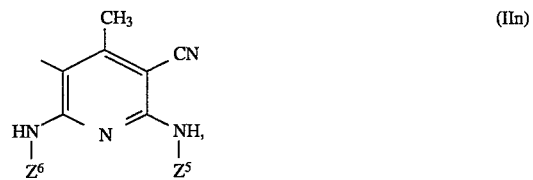

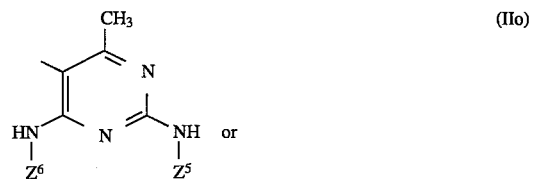

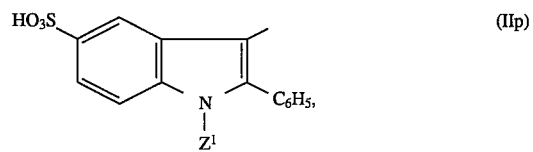

where $Z^1$, $Z^5$ and $Z^5$ are each as defined above.

Of technical interest are benzophenoneazo dyes of the formula Ig

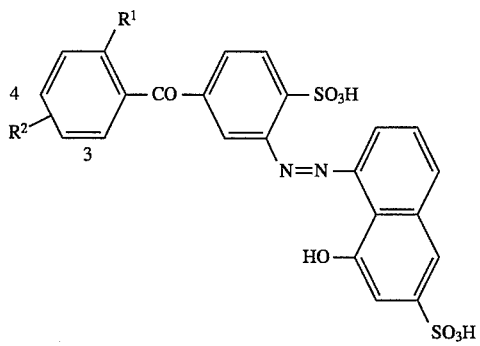

where $R^1$ is hydrogen, $C_1$–$C_3$-alkyl or $C_1$–$C_4$-alkoxy, and $R^2$ is $C_1$–$C_{12}$-alkyl, benzyl, phenylethyl or $C_1$–$C_4$-alkoxy in ring portion 3 or 4, with the proviso that the total number of carbon atoms in the radicals $R^1$ and $R^2$ is from 4 to 12.

The novel aminobenzophenones of the formula I can be obtained in a conventional manner.

For example, an aminobenzophenone of the formula III

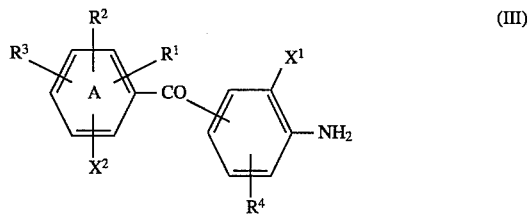

where $R^1$, $R^2$, $R^3$, $R^4$, $X^1$, $X^2$ and the ring A are each as defined above, is diazotized in a conventional manner and coupled with a coupling component of the formula IV

where K and Y are each as defined above. When m in the formula I is 2 and K—Y is the radical of a bivalent coupling component of the formula IId, generally twice the amount is used of the diazonium salt obtainable from the aminobenzophenone III.

When Y in the formula I is the radical $Q^1$—N=N—, the novel dyes can be obtained for example by first coupling the diazonium salt of the amine of the formula V $Q^1$—$NH_2$     (V)

where $Q^1$ is as defined above, with the coupling component of formula IVa

where K is as defined above, and coupling the resulting monoazo dye of the formula VI

where $Q^1$ and K are each as defined above, with the diazonium salt of the aminobenzophenone III. However, it is also possible to carry out the coupling reactions in the reverse order.

It is further possible to replace the amine of the formula V by an aminobenzophenone of the formula III, in which case the disazo dye obtained contains two different or identical radicals of the diazo component of the formula III.

If the coupling component of the formula IVa is of the aniline or naphthalene series (formula III or IIm) and if it contains an unsubstituted amino group or a precursor thereof, the resulting monoazo dye of the formula VII

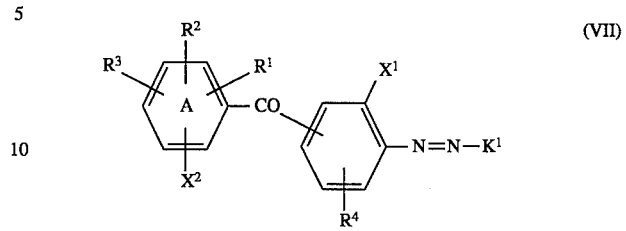

where $K^1$ is the radical of a coupling component of the aniline or naphthalene series which has an amino group, and $R^1$, $R^2$, $R^3$, $R^4$, $X^1$, $X^2$ and the ring A are each as defined above, can also e diazotized again and coupled with a coupling component of the formula IVa. This again leads to disazo dyes.

The aminobenzophenones of the formula III are known compounds. They are described for example in the earlier European Patent Application No. 91112002.0.

The coupling components of the formula IV are likewise known products. They are described for example in D. R. Waring, G. Hellas, The Chemistry and Application of Dyes, Plenum Press, New York, 1990, or M. Okawara, T. Kitao, T. Hirashima, M. Matsuoka, Organic Colorants, Elsevier, Amsterdam, 1988, or in the references cited therein.

The present invention also provides novel pyridone compounds of the formula II

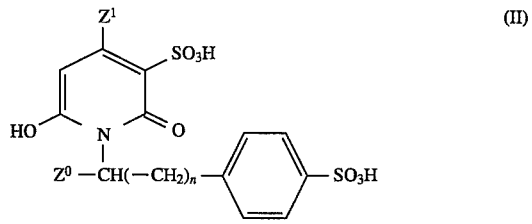

where n is 1 or 2, $Z^0$ is hydrogen or $C_1$–$C_4$-alkyl, and $Z^1$ is hydrogen, $C_1$–$C_4$-alkyl or phenyl.

Preference is given to pyridone compounds of the formula II where n is 1, $Z^1$ is $C_1$–$C_4$-alkyl, in particular methyl, and $Z^0$ is hydrogen or methyl, in particular methyl.

Monosulfonic acids of a similar kind are known from DE-A-2,117,753.

The pyridone compounds II are highly suitable for use as a coupling components for preparing azo dyes.

They can be obtained by reacting for example a hydroxypyridone of the formula VIII

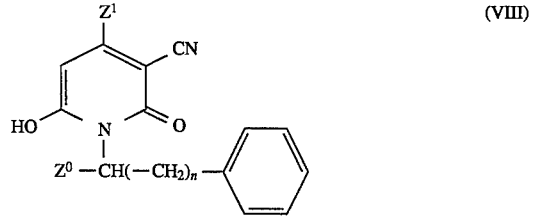

where n, $Z^0$ and $Z^1$ are each as defined above, in a baking process or with concentrated sulfuric acid in a two-stage reaction in a one-pot process in the presence or absence of oleum. In general, the first stage is carried out at from 30° to 70° C. and the second at from 120° to 150° C.

It has also been found that the preparation of the pyridone compounds of the formula IIa $$\text{(IIa)}$$

[Structure: pyridone with $Z^1$ at position 4, $SO_3H$ at position 3, HO at position 6, N substituted with $Z^0-CH(-CH_2)_a-$phenyl$-SO_3H$, carbonyl at position 2]

where a is 0, 1 or 2, $Z^0$ is hydrogen or $C_1$–$C_4$-alkyl and $Z^1$ is hydrogen, $C_1$–$C_4$-alkyl or phenyl, by reaction of pyridones of the formula IIb $$\text{(IIb)}$$

[Structure: pyridone with $Z^1$ at position 4, $W^4$ at position 3, HO at position 6, N substituted with $Z^0-CH(-CH_2)_a-$phenyl, carbonyl at position 2]

where $W^4$ is cyano or acetyl and a, $Z^0$ and $Z^1$ are each as defined above, with oleum is particularly successful on using oleum which contains from 1 to 2 mol of free sulfur trioxide and carrying out the reaction in a first stage at from 0° to 75° C. for from 1 to 5 hours and then in a second stage at from 80° to 135° C. for from 2 to 11 hours.

In this process, the sulfonic acid group goes into the phenyl ring in the first stage and into the pyridine ring in the second stage.

The reaction mixture is worked up in a conventional manner, for example by stirring out onto ice-water and subsequent neutralization, for example with sodium hydroxide solution.

The oleum used is advantageously a product which contains from 1 to 2 mol, preferably from 1 to 1.5 mol, of free sulfur trioxide.

The molar ratio of oleum:pyridone IIb is in general from 0.5:1 to 0.55:1, preferably from about 0.51:1.

It is also possible to use more oleum or oleum having a higher sulfur trioxide content, but this does not yield any further benefits. On the contrary, distinctly more ice-water and sodium hydroxide solution is required in the subsequent working up of th reaction mixture.

The novel benzophenoneazo dyes of the formula I are advantageously suitable for dyeing natural or synthetic substrates, for example wool, leather or polyamide. The dyes obtained have good general use fastness properties.

They are also suitable for the ink jet process.

The following Examples further illustrate the invention:

EXAMPLE 1

21.2 g of the diazo component of the formula $$H_2N-\text{C}_6H_4-\overset{O}{\overset{\|}{C}}-\text{C}_6H_4-CH_2CH_2-\text{C}_6H_4-\overset{O}{\overset{\|}{C}}-\text{C}_6H_4-NH_2$$

were suspended with 60 ml of concentrated hydrochloric acid, 60 ml of glacial acetic acid and 0.2 g of an acidic wetting agent. The mixture was then cooled down to 0° C., and 31 ml of 23% strength by weight aqueous sodium nitrite solution were added at from 0° to 6° C. Presently a clear diazonium salt solution was obtained, which was subsequently stirred at from 0° to 6° C. for 2 hours. Excess nitrous acid was then destroyed with sulfamic acid. Then this mixture was mixed with 35.6 g of the coupling component of the formula

[Structure: pyridone with $CH_3-C(=O)-$ at position 3, $CH_3$ at position 4, OH at position 6, N substituted with $-CH_2CH_2-$phenyl$-SO_3H$]

which had beforehand been dissolved in 250 ml of water with 26 g of 50% strength by weight sodium hydroxide solution and cooled down to 0° C.

The coupling mixture was buffered at from 0° to 6° C. with sodium hydroxide solution at a ph of 3.5–4. The resulting dye of the formula $$\left[-CH_2-\text{C}_6H_4-\overset{O}{\overset{\|}{C}}-\text{C}_6H_4-N=N-\underset{\text{pyridone with }CH_3,\ COCH_3,\ HO,\ N-CH_2CH_2-C_6H_4-SO_3Na}{\phantom{X}}\right]_2$$

was precipitated with sodium chloride, filtered off with suction, dried and ground. 120 g were obtained of a yellow powder having a dye content of 50% by weight.

The absorption maximum of a dye solution in a mixture of 1 g of glacial acetic acid and 9 g of N,N-dimethylformamide is 428 nm.

The dye produces dyeings on leather, nylon and wool in a bright yellow shade of good and wet and light fastness.

EXAMPLE 2

Example 1 was repeated, except that the coupling component was replaced by 35.7 g of the coupling component of the formula

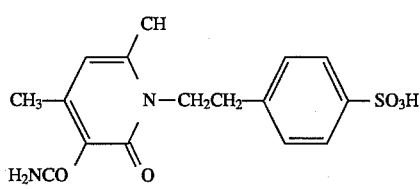

affording 59.5 g of the dye of the formula

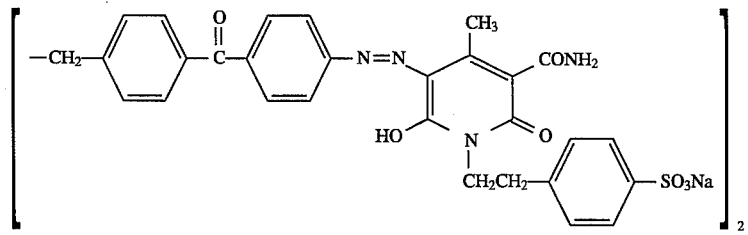

as a 50% strength by weight yellow powder whose absorption maximum in a solution of 9:1 g/g N,N-dimethylformamide/glacial acetic acid is 429 nm.

The dye gives deep bright yellow dyeings on wool and nylon having good fastness properties.

EXAMPLE 3

Example 1 was repeated, except that the coupling component was replaced by 20.5 g of the coupling component of the formula

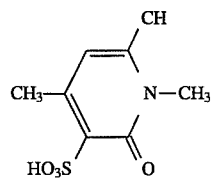

affording 42 g of the dye of the formula

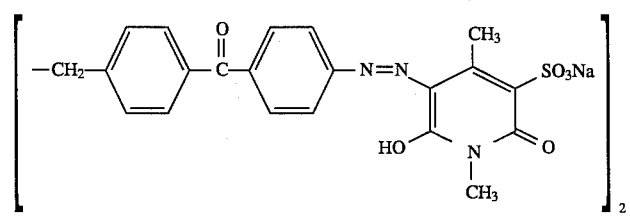

as a 90% strength by weight powder.

The dye produces bright yellow dyeings on nylon, wool and leather of good light fastness.

The ink jet process gives prints having good general use fastness properties.

The absorption maximum in water is 420 nm.

EXAMPLE 4

21.1g of the diazo component of the formula

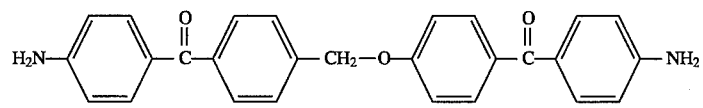

were diazotized by the method described in Example 1 and coupled in a similar manner to 20.5 g of 1,4-dimethyl-6-hydroxy-3-hydroxysulfonylpyrid-2-one, affording 42 g of the dye of the formula

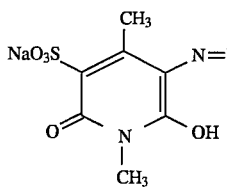

as a 90% strength by weight powder.

The dye produces bright yellow dyeings on leather, nylon and wool having good fastness properties.

The ink jet process gives prints having good general use fastness properties.

EXAMPLE 5

58 g of the diazo component of the formula

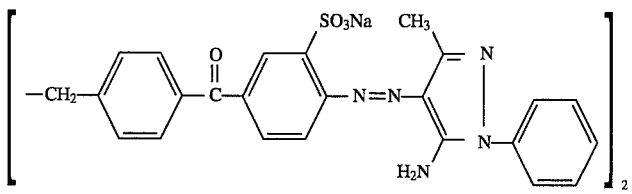

were suspended in 500 ml of water with 0.2 g of an acidic wetting agent. The pH of the mixture was then raised with 16.5 g of sodium hydroxide solution (50% strength by weight) to 8.5–11.5, at which point 62 ml of 23% strength by weight aqueous sodium nitrite solution were added. This mixture was added to a mixture of 70 ml of concentrated hydrochloric acid and ice in such a way that the temperature of the diazonium salt mixture stayed below 8° C. at all times. The diazonium salt suspension was subsequently stirred at from 0° to 6° C. for 4 hours. Excess nitrous acid was then destroyed in a conventional manner, a solution of 34.6 g of 1-phenyl-3-methyl-5-aminopyrazole in dilute hydrochloric acid was added, and the pH of the reaction mixture was gradually raised to from 2.3 to 3.1. It was subsequently stirred overnight at pH 3. The resulting dye of the formula was isolated in a conventional manner. 116 g were obtained of an orange 80% strength by weight powder. The dye produces fast reddish yellow dyeings on wool and nylon.

EXAMPLE 6

29.1 g of 4-amino-4'-methylbenzophenone-3-sulfonic acid were dissolved in 200 ml of water at pH 8–11 with sodium hydroxide solution. 31 ml of 23% strength by weight aqueous sodium nitrite solution were added. The solution was then discharged with stirring onto a mixture of 32 ml of concentrated hydrochloric acid and ice at a rate such that the temperature did not exceed +8° C. The suspension was subsequently stirred at 0°–5° C. for 3 hours. Excess nitrous acid was then destroyed with sulfamic acid, at which point 17.3 g of 1-phenyl-3-methyl-5-amino-pyrazole, dissolved in 300 ml of water and 10 ml of concentrated hydrochloric acid, were added.

The pH of the mixture was then raised with sodium hydroxide solution and a little sodium formate to 2.6–3.5. Coupling was complete after about 2 hours. To crystallize the dye of the formula

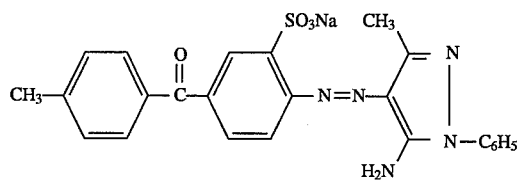

the reaction mixture was seeded and stirred overnight. The product was isolated and dried in a conventional manner, affording 54 g of an orange powder having a dye content of 91% by weight (remainder: water and sodium chloride).

The dye produces uniform dyeings on nylon and wool in a deep reddish yellow shade of excellent light fastness. Migration is also excellent.

EXAMPLE 7

58 g of the diazo component mentioned in Example 6 were diazotized with 62 ml of sodium nitrite as described in Example 6. The suspension obtained was admixed with 41 g of a thoroughly dispersed aqueous suspension of the coupling component of the formula

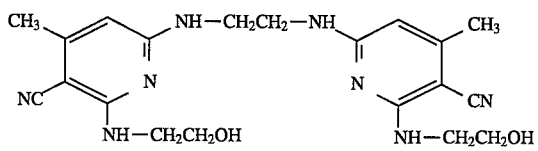

The reaction mixture was then left to stir overnight at room temperature at a pH of 2.8–3.3. The resulting dye of the formula

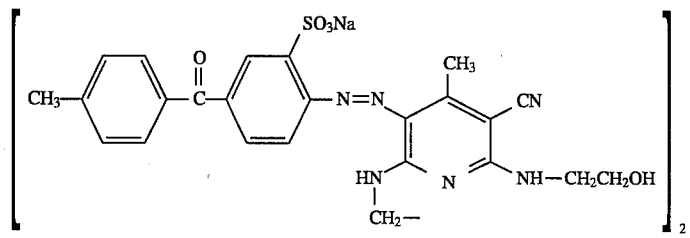

was precipitated with sodium chloride and then isolated, dried and ground in a conventional manner. This gave 105 g of the dye in the form of an 80% strength by weight powder.

The absorption maximum of the dye in aqueous solution is 460 nm.

The dye produces bright reddish orange dyeings on nylon, wool and leather of good to very good fastness.

EXAMPLE 8

30.5 g of the diazo component 4-amino-2',4'-dimethylbenzophenone-3-sulfonic acid were diazo-tized as described in Example 7. The diazonium salt suspension was mixed with 23.6 g of a suspension of the coupling component of the formula

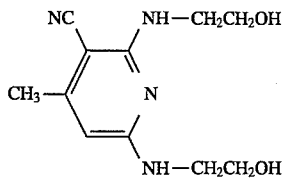

The pH of the reaction mixture was gradually raised with sodium hydroxide solution to 3.5 until the coupling had ended. Then it was adjusted to pH 7 with sodium hydroxide solution and evaporated to dryness.

This gave 78 g of a red powder (dye content: 57.4 g) which produces orange dyeings on nylons and wool having very good fastness properties. The leveling power of the dye (migration) is good. The dye has the formula

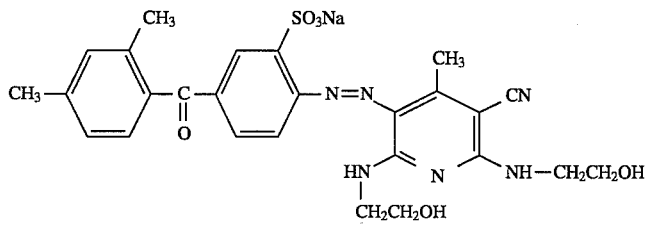

It absorption maximum in water is 457 nm.

EXAMPLE 9

30.7 g of the diazo component 4-amino-4'-methoxybenzophenone-3'-sulfonic acid were diazotized as described in Example 6. The resulting suspension of the diazonium salt was admixed with 17.3 g of 1-phenyl-3-methyl-5-aminopyrazole, dissolved in 150 ml of water with 9 ml of concentrated hydrochloric acid. The pH of the reaction mixture was then gradually raised to 2.6–3.5 and subsequently stirred at pH 3–3.5 for 2 hours. The dye of the formula

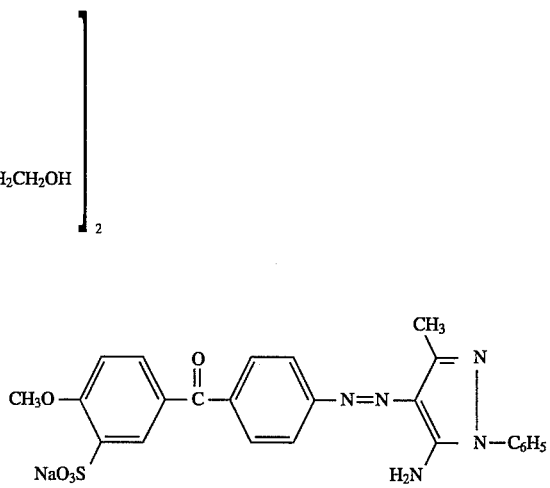

was stirred out with sodium chloride and isolated, dried and ground in a conventional manner. This gave 51.2 g of the dye in the form of a 75% strength by weight yellow powder.

The dye has high affinity for nylon and wool and levels out differences in material in particular in the case of nylon. Its migration and light fastness properties on nylon are good. Nylon and wool are dyed a greenish yellow.

EXAMPLE 10

29.1 g of 4-amino-4'-methylbenzophenone-3'-sulfonic acid were diazontized as described in Example 6. After excess nitrous acid had been destroyed, the suspension of the diazonium salt was combined with a freshly prepared fine suspension of 31.9 g of 1-hydroxy-8-aminonaphthalene-3, 6-disulfonic acid which was acidified with hydrochloric acid to pH 0.5–0. The reaction mixture was left to stir overnight at 5°–10° C., producing a red dye of the formula

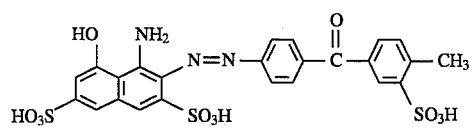

$\lambda_{max}$ (water):601 nm

The dye was precipitated in full with sodium chloride and isolated in a conventional manner. The product thus isolated was dissolved with sodium hydroxide solution in 1000 ml of water at pH 6–9. The solution was then admixed with 0.1 mol of diazotized 4-amino-2',5'-dimethylbenzophenone, and the pH of the reaction mixture was maintained at >6–8. The resulting dye of the formula

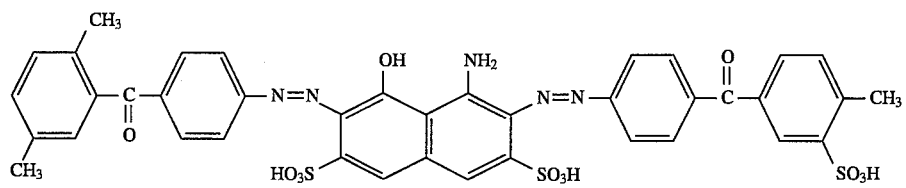

was precipitated with sodium chloride at pH 6–8 in the form of the trisodium salt and isolated in a conventional manner.

This gave 120 g of a black powder which dyes leather, nylon and wool in a navy shade. The dye still contains about 24 g of sodium chloride.

The absorption maximum of the dye in water is 604 nm.

The same method was used to obtain the dyes listed below.

TABLE 1

$$\left[ K-N=N-\underset{\underset{O}{\parallel}}{\overset{}{C}}\text{(phenylene)}-\overset{O}{\overset{\parallel}{C}}-\text{(phenylene)}-CH_2- \right]_2$$

| Example No. | K | E | G | Hue | $\lambda_{max}$ [nm] |
|---|---|---|---|---|---|
| 11 | pyridone with CH$_3$, OH, N-G-C$_6$H$_4$-SO$_3$H, E | CONH$_2$ | CH$_2$ | bright yellow | |
| 12 | pyridone with CH$_3$, OH, N-G-C$_6$H$_4$-SO$_3$H, E | COCH$_3$ | CH$_2$ | bright yellow | |
| 13 | pyridone with CH$_3$, OH, N-G-C$_6$H$_4$-SO$_3$H, E | COCH$_3$ | CH$_2$-CH(CH$_3$) | bright yellow | |
| 14 | pyridone with CH$_3$, OH, N-G-C$_6$H$_4$-SO$_3$H, E | COCH$_3$ | CH$_2$CH$_2$CH$_2$ | bright yellow | |
| 15 | pyridone with CH$_3$, OH, N-G-C$_6$H$_4$-SO$_3$H, E | CONH$_2$ | CHCH$_2$(CH$_3$) | bright yellow | |

TABLE 1-continued
$$\left[ K-N=N-\underset{\underset{O}{\parallel}}{\bigcirc}-\overset{O}{\underset{\parallel}{C}}-\bigcirc-CH_2- \right]_2$$
| Example No. | K | E | G | Hue | $\lambda_{max}$ [nm] |
|---|---|---|---|---|---|
| 16 | 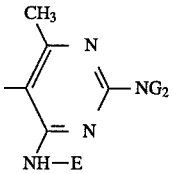 | 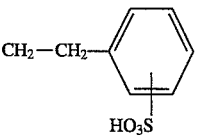 | $C_2H_5$ | yellow | |
| 17 | 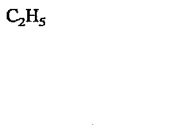 | $CH_3$ | 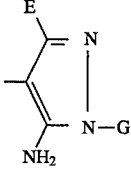 | greenish yellow | |
| 18 |  | H | 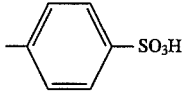 | greenish yellow | |
| 19 | 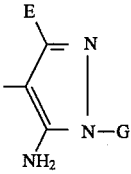 | — | — | yellowish | |
| 20 |  | — | — | red | 509 (in water) |
| 21 | 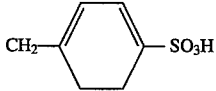 | — | — | yellow | |

TABLE 2

Diazo component:

R¹, R², R³-substituted benzophenone with SO₃K and N=N-K azo group

| Example No. | K | R¹ | R² | R³ | G¹ | G² | Hue |
|---|---|---|---|---|---|---|---|
| 22 | pyridine ring: NH—G¹, CH₃, CH₃, NC, NH—G² | H | CH₃ | SO₃H | C₂H₅ | C₂H₅ | orange |
| 23 | pyridine ring: NH—G¹, CH₃, CH₃, NC, NH—G² | H | CH₃ | SO₃H | C₂H₄—C₆H₅ | C₂H₄OH | orange |
| 24 | pyridine ring: NH—G¹, CH₃, CH₃, NC, NH—G² | H | CH₃ | H | (CH₂)₃OH | (CH₂)₃OH | orange |
| 25 | pyridine ring: NH—G¹, CH₃, CH₃, NC, NH—G² | H | OCH₃ | H | (CH₂)₃OCH₃ | (CH₂)₃OCH₃ | orange |
| 26 | pyridine ring: NH—G¹, CH₃, CH₃, NC, NH—G² | H | OCH₃ | H | C₂H₄—C₆H₄—SO₃H | C₂H₄OH | orange |
| 27 | pyridine ring: NH—G¹, CH₃, CH₃, NC, NH—G² | H | OCH₃ | H | C₂H₄—C₆H₄—SO₃H | C₄H₉(n) | orange |
| 28 | pyridine ring: NH—G¹, CH₃, CH₃, NC, NH—G² | CH₃ | OCH₃ | H | C₂H₄—C₆H₄—SO₃H | C₂H₄OH | orange |

TABLE 2-continued
Diazo component:
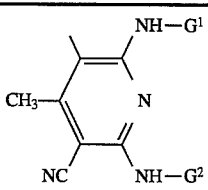
| Example No. | K | R¹ | R² | R³ | G¹ | G² | Hue |
|---|---|---|---|---|---|---|---|
| 29 |  | CH₃ | H | CH₃ | 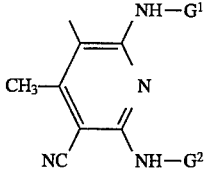 | C₂H₄OH | orange |
| 30 | 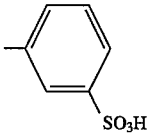 | CH₃ | H | CH₃ | 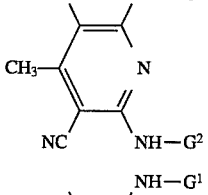 | C₂H₄OH | reddish orange |
| 31 | 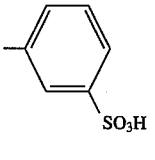 | CH₃ | H | CH₃ | 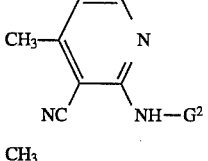 | C₄H₉(n) | reddish orange |
| 32 | 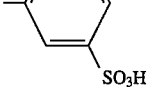 | H | C₂H₅ | H | 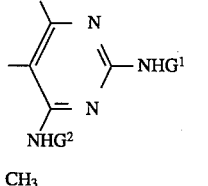 | C₄H₉(n) | reddish orange |
| 33 | 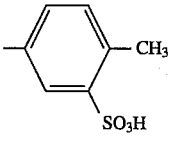 | H | CH₃ | H | 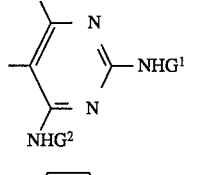 | C₄H₉(n) | yellow |
| 34 | 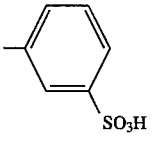 | CH₃ | CH₃ | H | 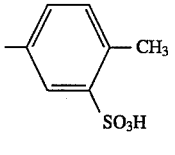 | C₄H₉(n) | yellow |
| 35 | 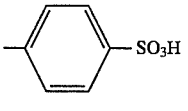 | CH₃ | H | CH₃ |  | C₄H₉(n) | yellow |

TABLE 2-continued

Diazo component:

structure: benzophenone with R¹ (ortho), R² (para), R³ (meta) on one ring; other ring has SO₃K and N=N–K with azo linkage

| Example No. | K | R¹ | R² | R³ | G¹ | G² | Hue |
|---|---|---|---|---|---|---|---|
| 36 | pyrazole with G¹, NH₂, N–G² substituents | H | CH₃ | H | H | –CH₂–C₆H₄–SO₃H | yellow |
| 37 | pyrazole with G¹, NH₂, N–G² substituents | CH₃ | CH₃ | H | H | –CH₂–C₆H₄–SO₃H | yellow |
| 38 | pyrazole with G¹, NH₂, N–G² substituents | CH₃ | CH₃ | H | CH₃ | –C₆H₄–SO₃H | yellow |
| 39 | pyrazole with G¹, NH₂, N–G² substituents | H | Cl | H | CH₃ | C₆H₅ | yellow |
| 40 | aniline with G¹, G², NH₂ substituents | H | OCH₃ | H | OCH₃ | OCH₃ | orange |
| 41 | aniline with G¹, G², NH₂ substituents | H | OCH₃ | H | OCH₃ | OCH₃ | orange |
| 42 | aniline with G¹, G², NH₂ substituents | H | OCH₃ | H | CH₃ | CH₃ | orange |

TABLE 3

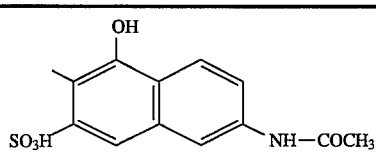

| Example No. | R¹ | R² | R³ | X¹ | R⁵ | R⁶ | R⁷ | R⁸ |
|---|---|---|---|---|---|---|---|---|
| 43 | H | CH₃ | CH₃ | H | SO₃H | H | OCH₃ | H |
| 44 | CH₃ | CH₃ | H | H | SO₃H | H | OCH₃ | H |
| 45 | H | CH₃ | CH₃ | H | SO₃H | H | CH₃ | H |
| 46 | H | CH₃ | H | H | SO₃H | H | CH₃ | H |
| 47 | H | CH₃ | CH₃ | H | H | H | OCH₃ | SO₃H |
| 48 | CH₃ | CH₃ | H | H | H | H | OCH₃ | SO₃H |
| 49 | H | CH₃ | CH₃ | H | H | H | CH₃ | SO₃H |
| 50 | H | CH₃ | H | H | H | H | CH₃ | SO₃H |
| 51 | OCH₃ | H | CH₃ | H | H | CH₃ | CH₃ | SO₃H |
| 52 | H | CH₃ | H | SO₃H | H | OCH₃ | CH₃ | H |
| 53 | H | OCH₃ | H | SO₃H | H | H | OCH₃ | H |
| 54 | H | C₂H₅ | H | H | SO₃H | H | C₂H₅ | H |
| 55 | H | C₂H₅ | H | H | H | H | C₂H₅ | SO₃H |
| 56 | CH₃ | CH₃ | H | H | H | H | CH₃ | SO₃H |
| 57 | H | Cl | H | H | H | H | CH₃ | SO₃H |
| 58 | H | C₂H₅ | H | H | H | H | CH₃ | SO₃H |

TABLE 4

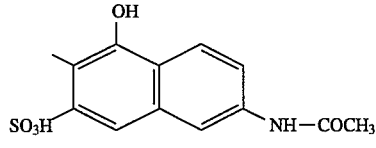

| Example No. | R¹ | R² | R³ | X¹ | X² | K | Hue |
|---|---|---|---|---|---|---|---|
| 59 | H | CH₃ | H | SO₃H | H | 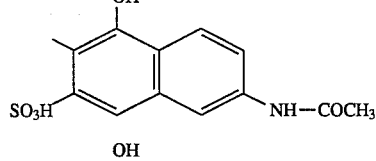 | orange |
| 60 | H | CH₃ | CH₃ | SO₃H | H | 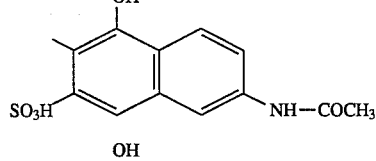 | orange |
| 61 | H | CH₃ | CH₃ | H | SO₃H | 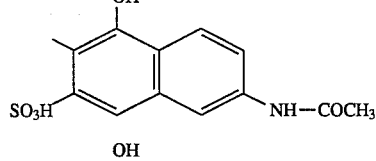 | orange |
| 62 | CH₃ | CH₃ | H | SO₃H | H | 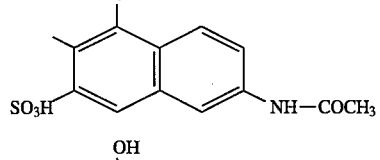 | orange |
| 63 | H | OCH₃ | H | SO₃H | H | 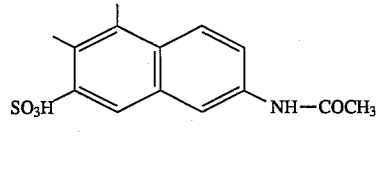 | orange |

TABLE 4-continued
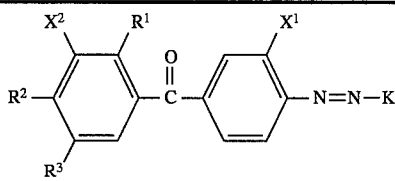
| Example No. | R¹ | R² | R³ | X¹ | X² | K | Hue |
|---|---|---|---|---|---|---|---|
| 64 | H | C₂H₅ | H | SO₃H | H | 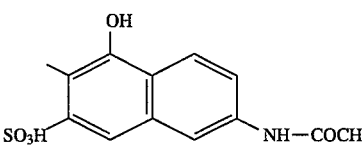 | orange |
| 65 | H | Cl | H | SO₃H | H | 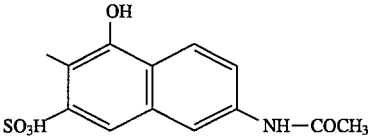 | orange |
| 66 | H | C₂H₅ | H | SO₃H | H | 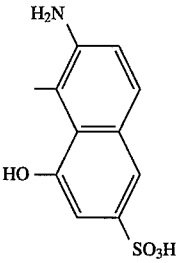 | red |
| 67 | H | CH₃ | H | SO₃H | H | 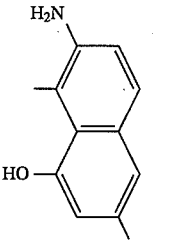 | red |
| 68 | H | OCH₃ | H | SO₃H | H | 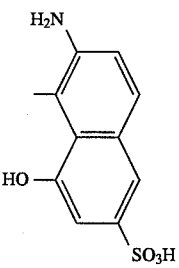 | red |
| 69 | H | OCH₃ | SO₃H | H | H | 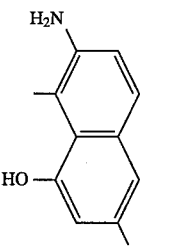 | red |

TABLE 4-continued
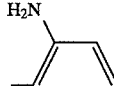
| Example No. | R¹ | R² | R³ | X¹ | X² | K | Hue |
|---|---|---|---|---|---|---|---|
| 70 | H | $C_2H_5$ | $SO_3H$ | H | H | 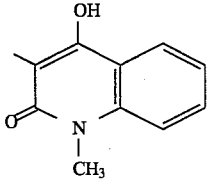 | red |
| 71 | H | $CH_3$ | $SO_3H$ | $SO_3H$ | H | 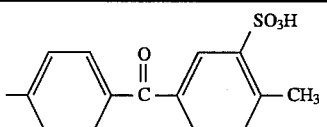 | yellow |
TABLE 5
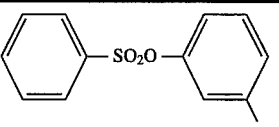
| Example No. | G¹ | G² | Hue |
|---|---|---|---|
| 72 | 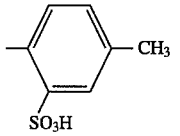 | 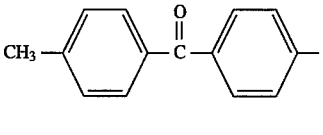 | blue |
| 73 | 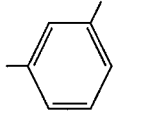 | 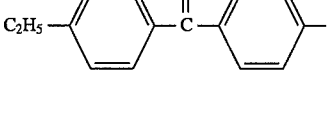 | blue |
| 74 | 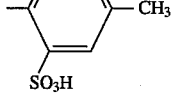 | 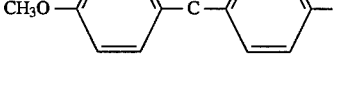 | blue |
| 75 | (structure with $CH_3$ and $SO_3H$) | (structure with $CH_3O$ and C=O linking phenyl groups) | blue |

TABLE 5-continued

Structure: Naphthalene core with OH, NH₂ substituents, bisazo (G²-N=N- and -N=N-G¹), and two HO₃S/SO₃H groups.

| Example No. | G¹ | G² | Hue |
|---|---|---|---|
| 76 | 4-(2-(benzothiazol-2-yl)phenyl with SO₃H and CH₃ substituents) | 4-(4-methoxybenzoyl)phenyl | bluish black |
| 77 | 4-(SO₂CH₂CH₂OSO₃H)phenyl | 4-(4-ethylbenzoyl)phenyl | bluish black |

TABLE 6

Structure: Benzophenone with R¹, R², R³, X² substituents on one ring; X¹, Cl, and -N=N-K on the other ring.

| Example No. | K | X¹ | R¹ | R² | R³ | X² | Hue or $\lambda_{max}$ [nm] |
|---|---|---|---|---|---|---|---|
| 78 | pyrazolone-type (CH₃, NH₂, N-C₆H₅) | H | H | CH₃ | OCH₃ | SO₃H | yellow |
| 79 | " | H | H | H | OCH₃ | SO₃H | yellow |
| 80 | " | H | H | H | OCH₃ | SO₃H | yellow |
| 81 | " | SO₃H | H | H | OCH₃ | H | yellow |
| 82 | pyridone (H₂NC(O), CH₃, N-C₂H₅, OH) | SO₃H | H | H | OCH₃ | H | greenish yellow |
| 83 | " | SO₃H | H | H | OCH₃ | H | greenish yellow |
| 84 | " | SO₃H | CH₃ | H | H | CH₃ | greenish yellow |
| 85 | pyridone (CH₃CO, CH₃, N-C₂H₅, OH) | SO₃H | H | H | CH₃ | H | greenish yellow |
| 86 | " | H | CH₃ | H | CH₃ | SO₃H | greenish yellow |
| 87 | " | H | H | H | C₂H₅ | SO₃H | greenish yellow |
| 88 | pyridone (CH₃CO, CH₃, N-C₂H₄-C₆H₄-SO₃H, OH) | H | H | H | CH₃ | H | greenish yellow |
| 89 | " | SO₃H | H | H | OCH₃ | H | greenish yellow |
| 90 | " | SO₃H | H | H | C₂H₅ | H | greenish yellow |
| 91 | " | SO₃H | H | H | CH(CH₃)₂ | H | greenish yellow |
| 92 | " | H | H | H | C₂H₅ | SO₃H | greenish yellow |

TABLE 6-continued

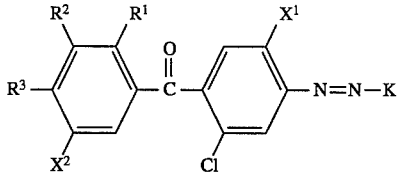

| Example No. | K | X¹ | R¹ | R² | R³ | X² | Hue or $\lambda_{max}$ [nm] |
|---|---|---|---|---|---|---|---|
| 93 | (pyridine structure with CH₃, CN, NH-C₂H₄OH groups) | SO₃H | OCH₃ | H | H | CH₃ | orange |
| 94 | | SO₃H | CH₃ | H | H | CH₃ | orange |
| 95 | | SO₃ | H | CH₃ | CH₃ | H | orange |
| 96 | (pyrimidine with CH₃, NH-C₃H₆OCH₃, NH-phenyl-SO₃H) | SO₃H | H | CH₃ | CH₃ | H | yellowish red |
| 97 | | SO₃H | H | H | C₂H₅ | H | yellowish red |
| 98 | | SO₃H | H | H | CH(CH₃)₂ | H | yellowish red |
| 99 | (pyrimidine with CH₃, N(C₄H₉)₂, NH-CH₂CH₂-phenyl-SO₃H) | SO₃H | H | H | C₃H₇(i) | H | orange |
| 100 | | SO₃H | H | CH₃ | CH₃ | H | orange |
| 101 | | SO₃H | H | H | C₂H₅ | H | orange |
| 102 | | SO₃H | CH₃ | H | CH₃ | H | orange |
| 103 | (naphthalene with NH₂, HO₃S) | SO₃H | H | H | C₃H₇(i) | H | 403 |
| 104 | | SO₃H | H | CH₃ | CH₃ | H | 404 |
| 105 | (naphthalene with OH, HO₃S, NHCOCH₃) | SO₃H | H | H | C₂H₅ | H | orange |
| 106 | | SO₃H | CH₃ | H | CH₃ | H | orange |
| 107 | (phenyl-N(C₂H₅)(CH₂-phenyl-SO₃H)) | SO₃H | H | H | CH₃ | H | yellowish red |
| 108 | | SO₃H | CH₃ | H | CH₃ | H | red |
| 109 | | SO₃H | H | H | C₂H₅ | H | yellowish red |
| 110 | (phenyl with NHCOCH₃, N(C₂H₅)(CH₂CH₂-phenyl-SO₃H)) | SO₃H | H | H | CH₃ | H | red |
| 111 | | SO₃H | H | H | OCH₃ | H | red |
| 112 | | SO₃H | CH₃ | H | H | CH₃ | red |

TABLE 6-continued

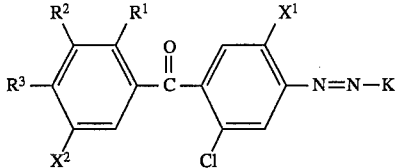

| Example No. | K | X¹ | R¹ | R² | R³ | X² | Hue or $\lambda_{max}$ [nm] |
|---|---|---|---|---|---|---|---|
| 113 | HN—C$_2$H$_4$OH | SO$_3$H | H | H | OCH$_3$ | H | orange |
| 114 | (see structure) | SO$_3$H | H | H | CH$_3$ | H | orange |

TABLE 7

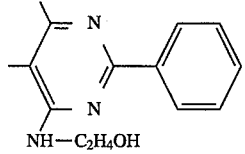

| Ex. No. | X¹ | R¹ | R² | R³ | R⁵ | R⁴ | G | $\lambda_{max}$ [nm] |
|---|---|---|---|---|---|---|---|---|
| 115 | H | H | H | CH$_3$ | H | H | CH$_3$ | 421 |
| 116 | H | H | H | C$_2$H$_5$ | H | H | CH$_3$ | 421 |
| 117 | H | H | CH$_3$ | CH$_3$ | H | H | CH$_3$ | 422 |
| 118 | H | CH$_3$ | H | CH$_3$ | H | H | CH$_3$ | 420 |
| 119 | H | OCH$_3$ | H | H | CH$_3$ | H | CH$_3$ | 422 |
| 120 | H | CH$_3$ | H | OCH$_3$ | H | H | C$_2$H$_5$ | 423 |
| 121 | H | H | H | CH$_3$ | H | Cl | CH$_3$ | 421 |
| 122 | H | H | H | C$_2$H$_5$ | H | Cl | CH$_3$ | 421 |
| 123 | H | H | H | OCH$_3$ | H | Cl | CH$_3$ | 422 |
| 124 | SO$_3$H | H | CH$_3$ | CH$_3$ | H | H | C$_2$H$_5$ | |
| 125 | SO$_3$H | CH$_3$ | H | CH$_3$ | H | H | C$_2$H$_5$ | |
| 126 | SO$_3$H | H | H | C$_2$H$_5$ | H | H | CH$_3$ | |
| 127 | SO$_3$H | H | H | C$_2$H$_5$ | H | Cl | CH$_3$ | |
| 128 | H | H | H | C$_2$H$_5$ | SO$_3$H | H | CH$_3$ | 421 |
| 129 | H | H | H | C$_2$H$_5$ | SO$_3$H | Cl | CH$_3$ | 421 |
| 130 | H | H | CH$_3$ | CH$_3$ | SO$_3$H | H | CH$_3$ | 421 |
| 131 | H | H | CH$_3$ | CH$_3$ | SO$_3$H | H | C$_4$H$_9$(n) | 421 |
| 132 | H | H | CH$_3$ | OCH$_3$ | H | Cl | CH$_3$ | 422 |
| 133 | SO$_3$H | H | CH$_3$ | CH$_3$ | H | OCH$_3$ | CH$_3$ | |
| 134 | H | H | H | CH$_3$ | H | OCH$_3$ | CH$_3$ | |

EXAMPLE 135

Brilliant greenish yellow on leather, nylon and wool.

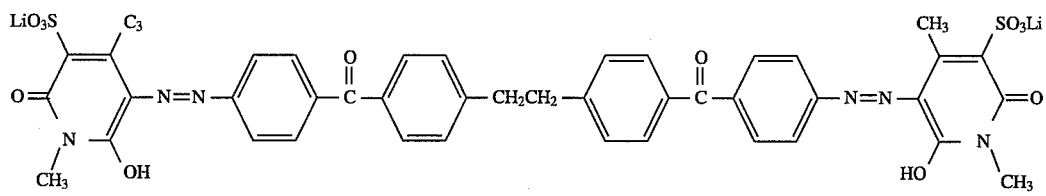

EXAMPLE 136
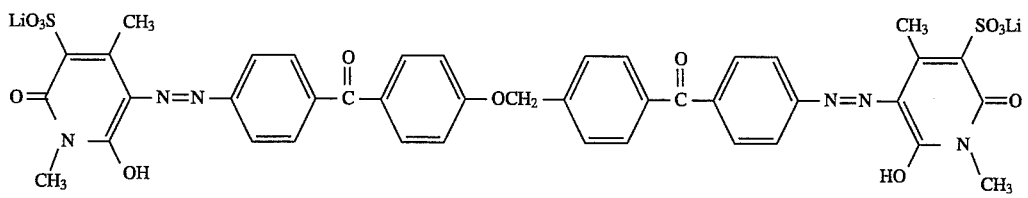
Bright greenish yellow on leather, nylon and wool.
EXAMPLE 137
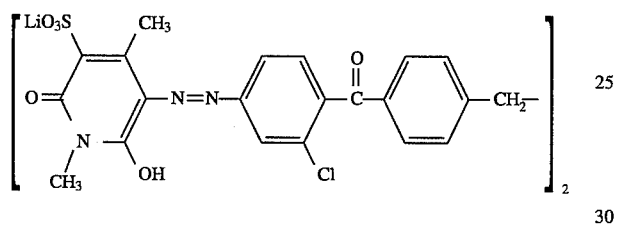
Greenish yellow on leather, nylon and wool.
EXAMPLE 138
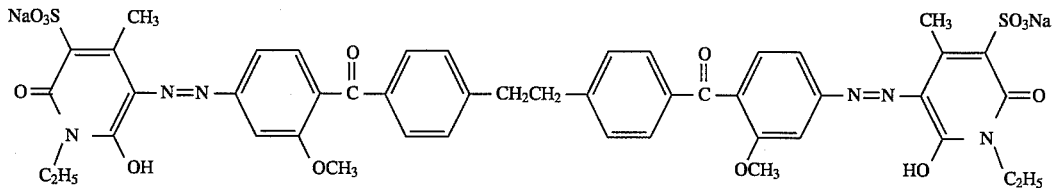
Greenish yellow on nylon, wool and leather.
EXAMPLE 139
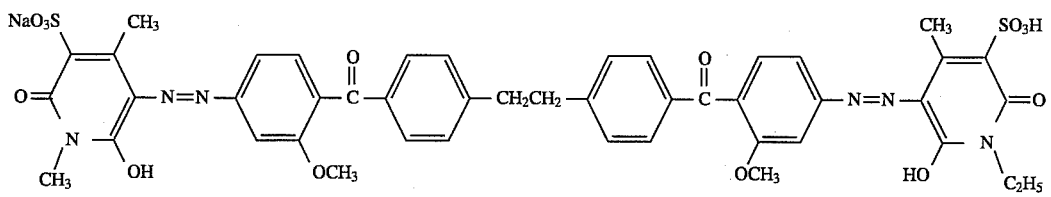
Greenish yellow on leather and wool.
EXAMPLE 140

EXAMPLE 140
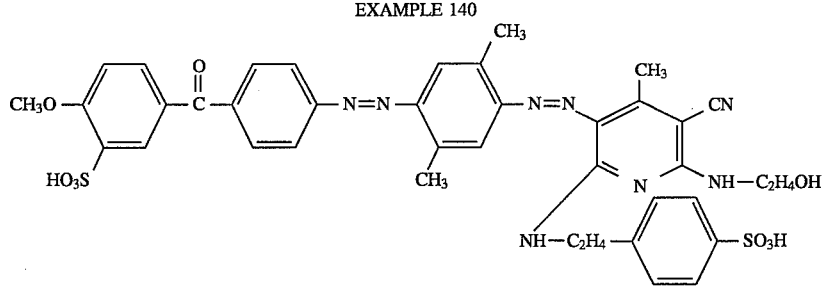
Hue red
EXAMPLE 141
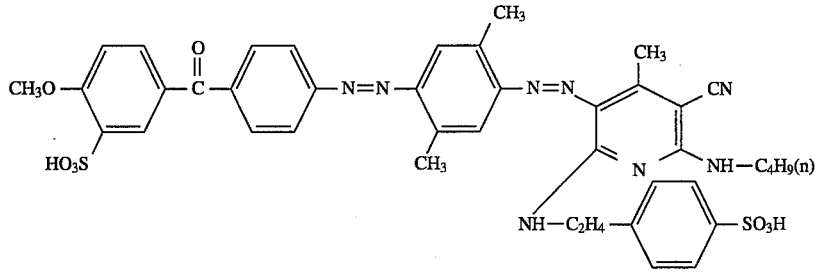
Hue red
EXAMPLE 142
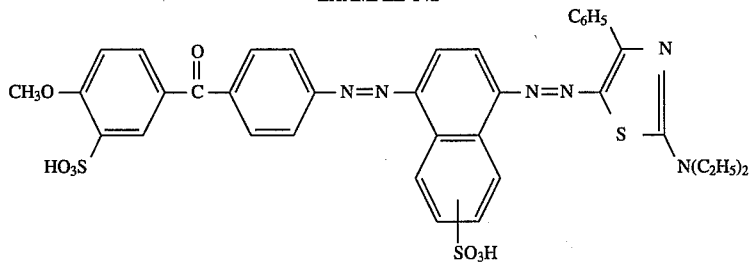
navy
EXAMPLE 143
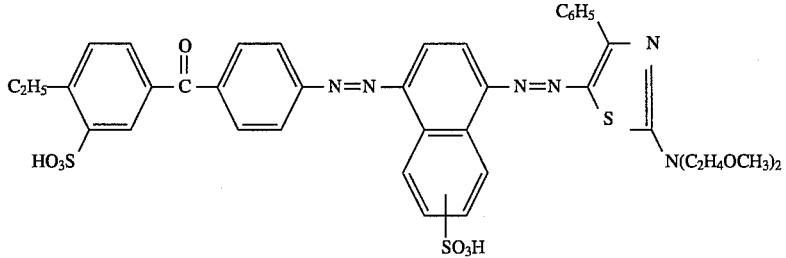
navy
EXAMPLE 144
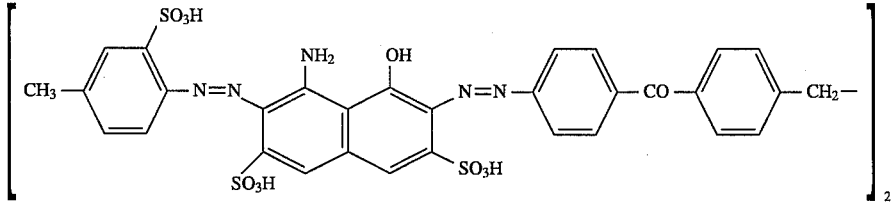
blue
EXAMPLE 145
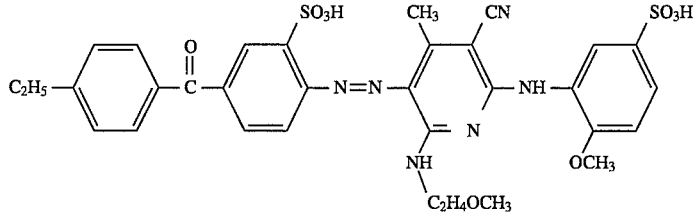
reddish orange
$\lambda_{max}$ (H$_2$O): 470 nm -continued
EXAMPLE 146
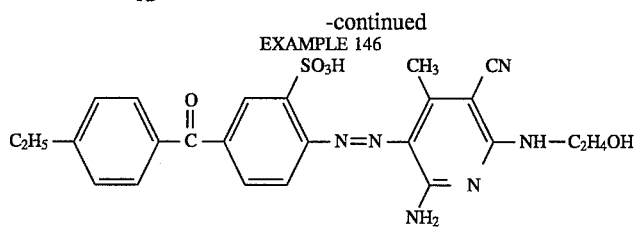
orange
EXAMPLE 147
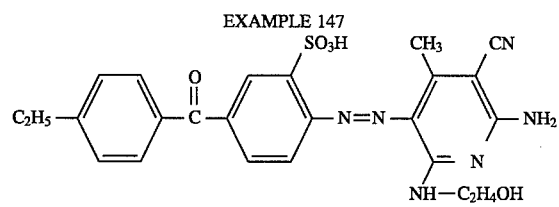
orange
EXAMPLE 148
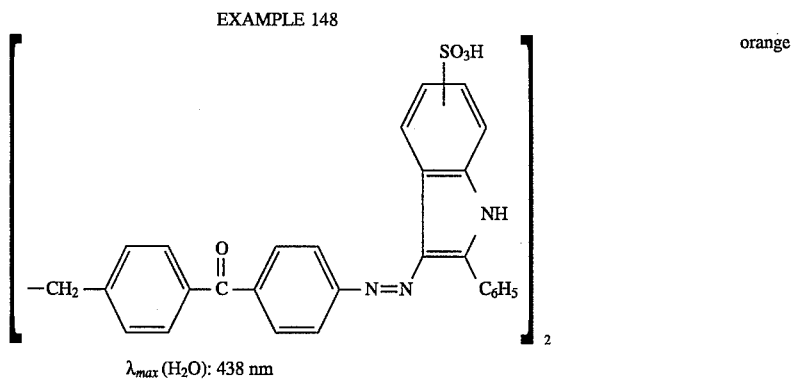
orange
$\lambda_{max}$ (H$_2$O): 438 nm
EXAMPLE 149
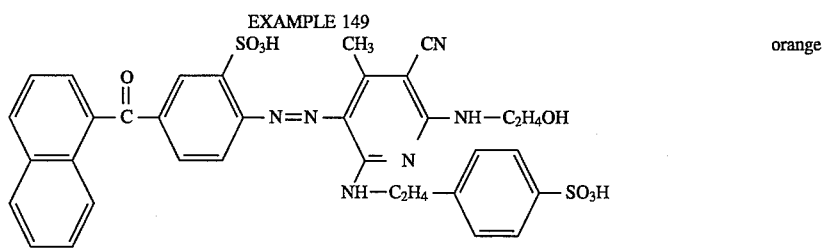
orange
EXAMPLE 150
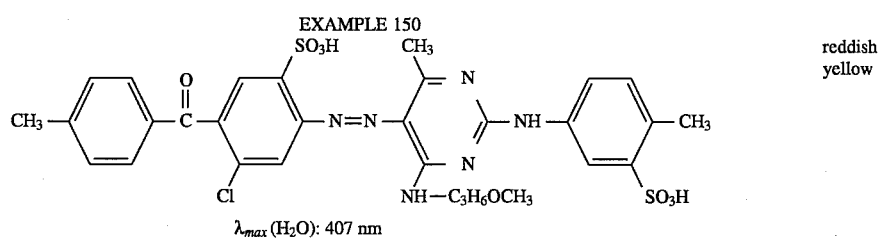
reddish yellow
$\lambda_{max}$ (H$_2$O): 407 nm
EXAMPLE 151
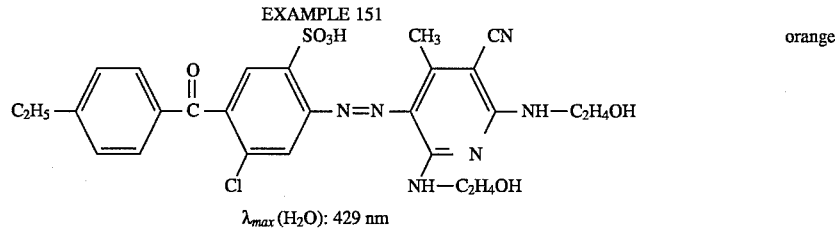
orange
$\lambda_{max}$ (H$_2$O): 429 nm -continued
EXAMPLE 152
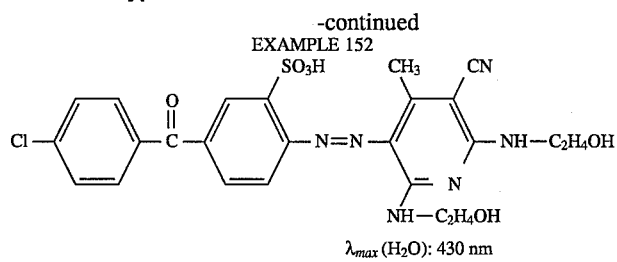
$\lambda_{max}$ (H$_2$O): 430 nm
orange
EXAMPLE 153
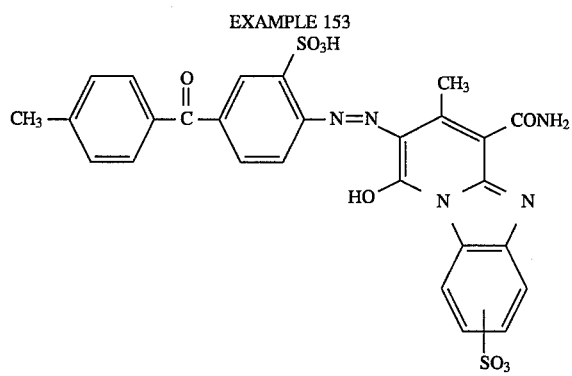
orange
EXAMPLE 154
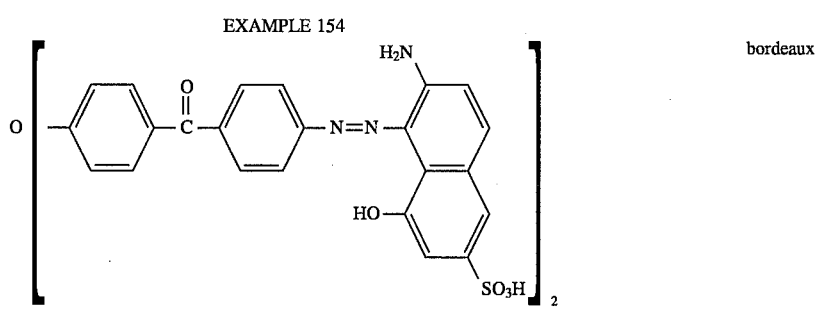
bordeaux
EXAMPLE 155
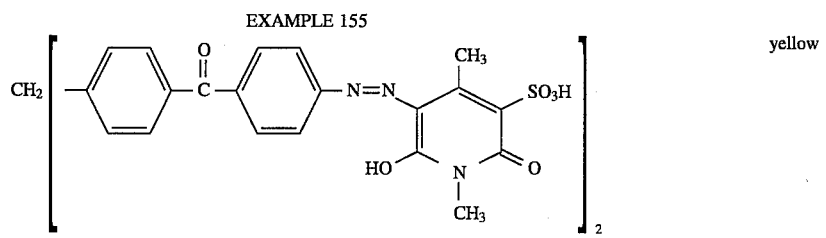
yellow
EXAMPLE 156
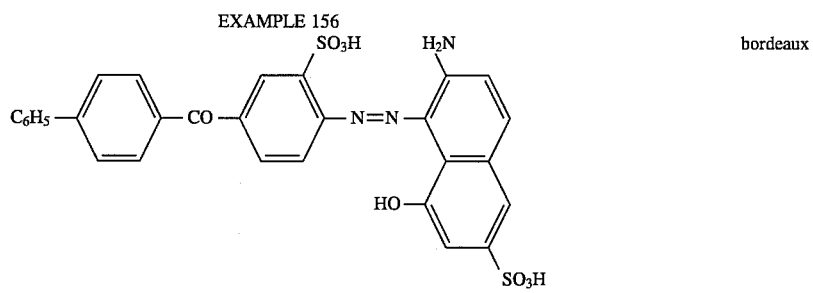
$\lambda_{max}$ (H$_2$O): 526 nm
bordeaux

EXAMPLE 157

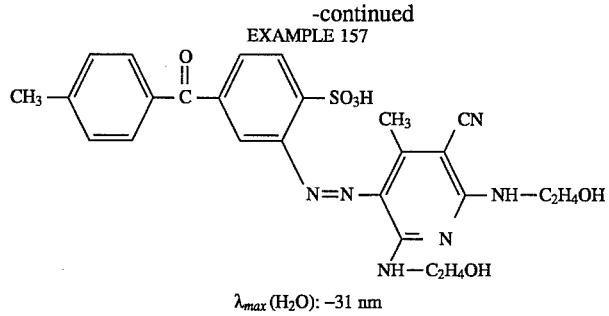

$\lambda_{max}$ (H$_2$O): –31 nm

EXAMPLE 158

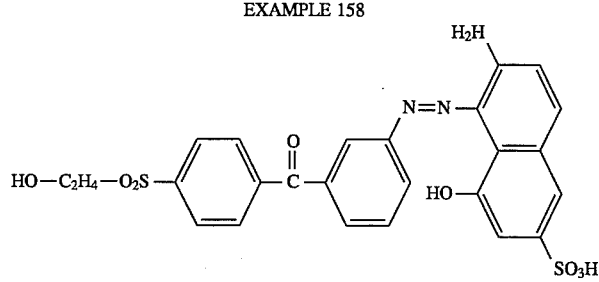

Hue
yellow red

TABLE 8

| Example No. | R$^1$ | R$^2$ | R$^3$ | Hue | $\lambda_{max}$ (H$_2$O) [nm] |
|---|---|---|---|---|---|
| 159 | H | CH$_3$ | H | bright red | 509 |
| 160 | H | C$_2$H$_5$ | H | bright red | 509 |
| 161 | H | CH(CH$_3$)$_2$ | H | bright red | 508 |
| 162 | CH$_3$ | CH$_3$ | H | bright red | 509 |
| 163 | CH$_3$ | H | CH$_3$ | bright red | 509 |
| 164 | H | CH$_3$ | CH$_3$ | bright red | 509 |
| 165 | H | C$_6$H$_5$ | H | bright red | 512 |
| 166 | H | Cl | H | bright red | 511 |
| 167 | H | CH$_3$ | Cl | bright red | 510 |

EXAMPLE 168 (use)

100 parts by weight of a retanned chrome leather having a shaved thickness of 1.4 mm were neutralized by drumming for 45 minutes in 200 parts by weight of water at 30° C. with 1 part by weight or sodium bicarbonate and 1 part by weight of sodium formate. The leather was then washed in 200 parts by weight of fresh water at 30° C. by drumming for 15 minutes. Thereafter the dyeing was effected by drumming for 45 minutes in 200 parts by weight of water at 50° C. containing 1% by weight of the dye described in Example 2. Then 4 parts by weight of a commercial fatliquor were added and drumming was continued for 30 minutes. After acidification with 0.5 part by weight of formic acid, the leather was drummed for a further 30 minutes and then rinsed with cold water, set out, dried, sawdusted, staked and strained.

The result obtained was leather dyed in a deep bright yellow shade having good light fastness and good wet fastness properties.

Similar results are obtained in the dyeing of leather with the dyes listed hereinafter.

TABLE 9

| Example No. | L$^1$ | X$^1$ | K | Hue |
|---|---|---|---|---|
| 169 | CH$_2$CH$_2$ | H | HO$_3$S-[indole-C$_6$H$_5$] | reddish yellow $\gamma_{max}$ (H$_2$O): 438 nm |

TABLE 9-continued
K—N=N—[Ar]—C(O)—[Ar]—L¹—[Ar]—C(O)—[Ar]—N=N—K
(with X¹ substituents)
| Example No. | L¹ | X¹ | K | Hue |
|---|---|---|---|---|
| 170 | CH₂CH₂ | H | 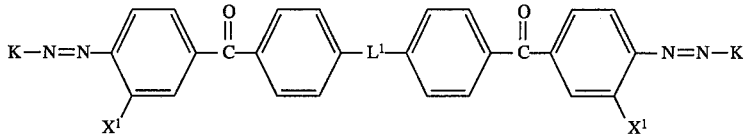 | greenish yellow |
| 171 | CH₂CH₂ | H | 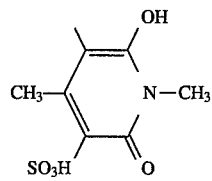 | greenish yellow |
| 172 | CH₂cH₂ | H | 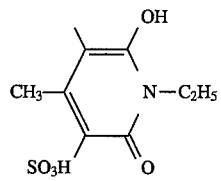 | greenish yellow |
| 173 | CH₂CH₂ | H | 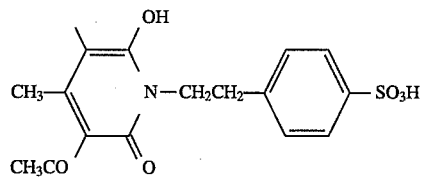 | greenish yellow |
| 174 | CH₂CH₂ | H | 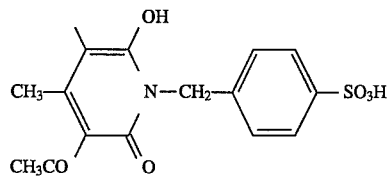 | greenish yellow |
| 175 | CH₂CH₂ | H | 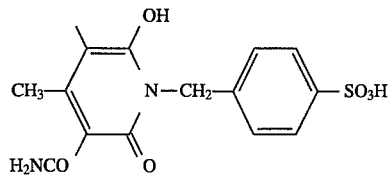 | greenish yellow |
| 176 | CH₂CH₂ | H | 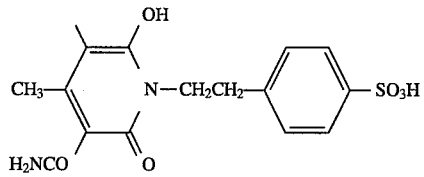 | greenish yellow |

TABLE 9-continued
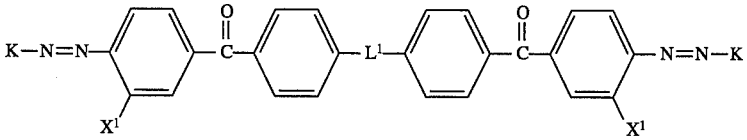
| Example No. | L¹ | X¹ | K | Hue |
|---|---|---|---|---|
| 177 | CH₂—O | H | 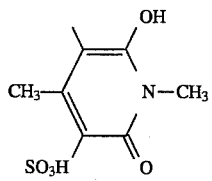 | greenish yellow |
| 178 | CH₂CH₂ | H | 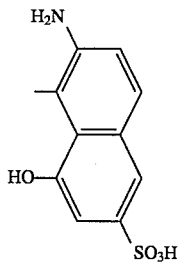 | bluish red $\gamma_{max}$(H₂O): 529 nm |
| 179 | CH₂CH₂ | H | 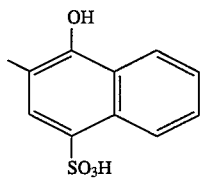 | orange |
| 180 | CH₂CH₂ | SO₃H | 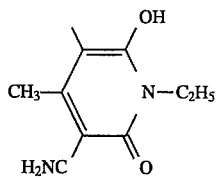 | greenish yellow |
| 181 | CH₂CH₂ | SO₃H | 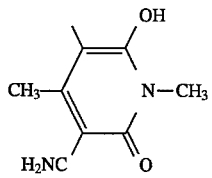 | greenish yellow |
| 182 | CH₂CH₂ | SO₃H | 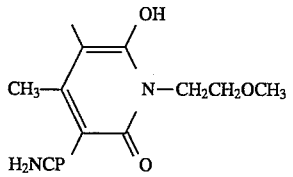 | greenish yellow |
| 183 | CH₂CH₂ | SO₃H | 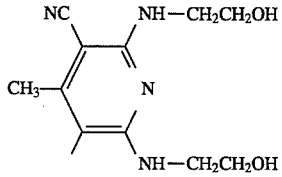 | reddish orange |

TABLE 10

[Structure: benzophenone with R¹, R² (ortho, para), R³ (meta) on one ring; other ring has SO₃H and N=N-K group]

| Example No. | R¹ | R² | R³ | K | Hue |
|---|---|---|---|---|---|
| 184 | H | CH₃ | H | [pyrimidine with CH₃, NH-C₂H₅, NH-phenyl-SO₃H] | reddish orange |
| 185 | H | CH₃ | H | [pyrimidine with CH₃, NH-C₃H₆OCH₃, NH-phenyl-SO₃H] | reddish orange |
| 186 | H | C₂H₅ | H | [pyrimidine with CH₃, NH-C₃H₆OCH₃, NH-phenyl-SO₃H] | reddish orange |
| 187 | H | CH₃ | CH₃ | [pyrimidine with CH₃, NH-C₃H₆OCH₃, NH-phenyl-SO₃H] | reddish orange |
| 188 | H | CH₃ | H | [pyridine with NC, CH₃, NH-CH₂CH₂C₆H₅, NH-CH₂CH₂-phenyl-SO₃H] | reddish orange |
| 189 | CH₃ | CH₃ | H | [pyrimidine with CH₃, N(C₄H₉)₂, HNCH₂CH₂-phenyl-SO₃H] | orange |
| 190 | H | (CH₃)₂CH | H | [pyridine with NC, CH₃, NHCH₂CH₂C₆H₅, NHCH₂CH₂-phenyl-SO₃H] | reddish orange |

TABLE 10-continued

[Structure with R¹, R², R³, SO₃H, and N=N-K groups on benzophenone]

| Example No. | R¹ | R² | R³ | K | Hue |
|---|---|---|---|---|---|
| 191 | H | CH₃ | H | [pyridone with NC, NH-(SO₃H-OCH₃ phenyl), CH₃, NHC₃H₆OCH₃] | yellowish red |
| 192 | H | C₆H₅ | H | [indole with HO₃S, CH₃, C₆H₅, NH] | orange |

EXAMPLE 193

42.1 g of the diazo component of the formula

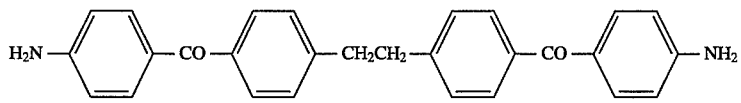

were slurried up at room temperature with 90 ml of 25% by weight hydrochloric acid and 10 drops of a wetting agent which is effective in an acid medium. 100 g of ice were added after 2 hours, followed with cooling by a total of 64 ml of 23% by weight aqueous sodium nitrite solution. The diazotization mixture was stirred at 0°–8° C. for 2.5 hours. All the excess nitrous acid was then destroyed with sulfamic acid and the resulting diazonium salt solution was diluted with 150 ml of ice-water. The mixture was then added to 65.1 g of the coupling component of the formula

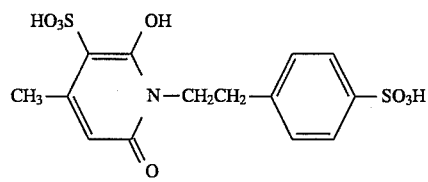

which had been dissolved at pH 7 in 300 ml or water and 300 ml of ice. During the addition of th diazonium salt solution the pH of the reaction mixture was maintained within the range from 4 to 7 with sodium hydroxide solution. The coupling reaction finished quickly. The honey yellow dye solution obtained was spray-dried at pH 4–6. This gave 122 g of the dye of the formula

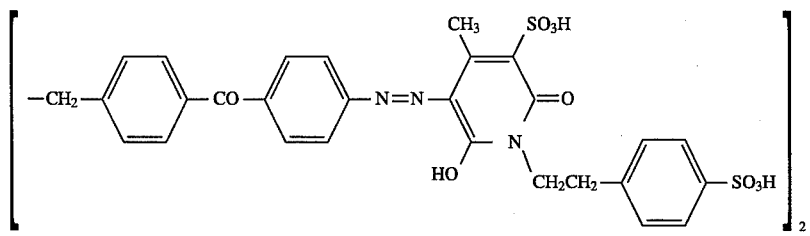

in the form of the sodium salt of the sulfonic acids. The yellow powder still contains sodium chloride.

From 0.5 to 1% strength dyeings of this dye on retanned leather produce a very bright, very highly wet-fast and light-fast greenish yellow. $\lambda_{max}$ (H$_2$O): 421 nm.

Replacing the abovementioned diazo components by a compound of the formula

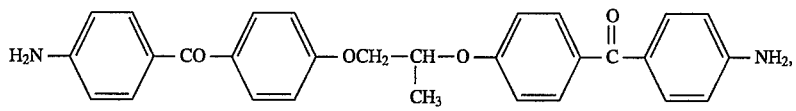

gives a yellow dye of the formula

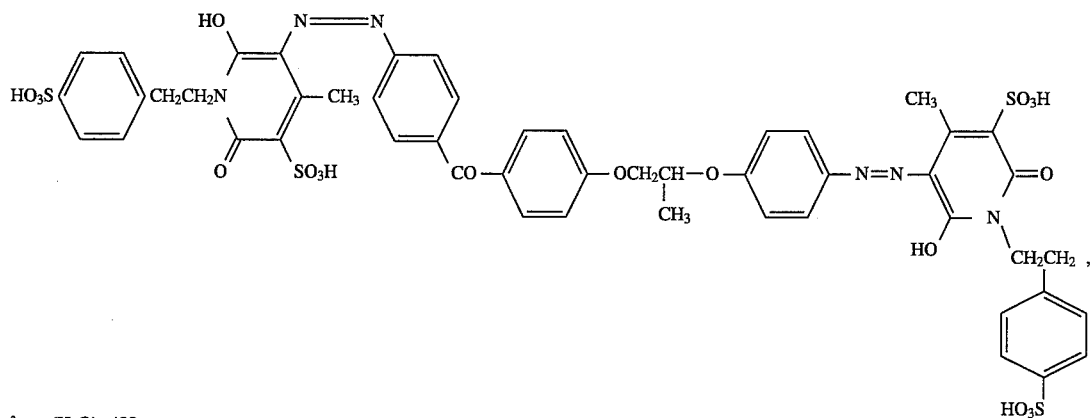

$\lambda_{max}$ (H$_2$O): 423nm which has a similar fastness profile.

The same method gives the following compounds and also the dyes listed in the following Tables 11 and 12:

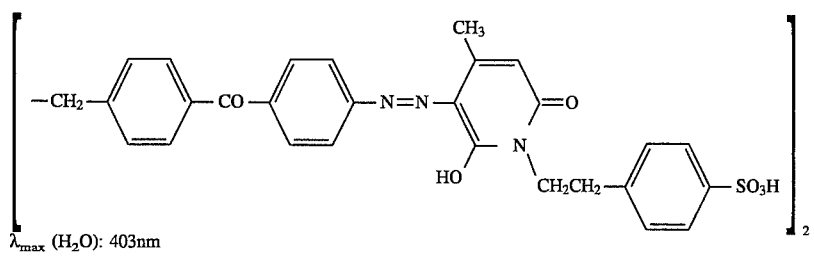

$\lambda_{max}$ (H$_2$O): 403nm

EXAMPLE 195

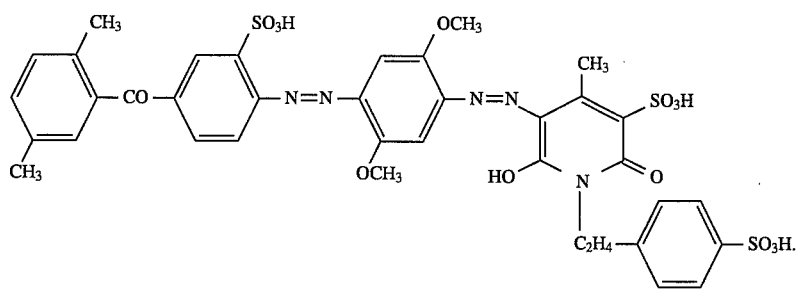

(Hue: red)

TABLE 11

[Structure: Q¹-C(=O)-C₆H₄-N=N-C(pyridone ring with CH₃, SO₃H, =O, OH substituents)-N-CH(Z°)-(CH₂)ₐ-C₆H₄-SO₃H]

| Example No. | Q¹ | Z° | a | λ_max [nm] (in water) | Hue |
|---|---|---|---|---|---|
| 196 | 2,4-dimethylphenyl | H | 1 | 431 | yellow |
| 197 | 2,4-diisopropylphenyl | H | 1 | 431 | yellow |
| 198 | biphenyl-4-yl | H | 1 | | yellow |
| 199 | 4-cyclohexylphenyl | H | 1 | 431 | yellow |
| 200 | naphthalen-1-yl | H | 1 | | yellow |
| 201 | acenaphthenyl | H | 1 | | yellow |
| 202 | $C_6H_5-$ | H | 1 | | greenish yellow |
| 203 | 4-methylphenyl | H | 1 | 431 | greenish yellow |
| 204 | 4-ethylphenyl | H | 1 | 432 | greenish yellow |
| 205 | 4-isopropylphenyl | H | 1 | 432 | greenish yellow |
| 206 | 4-chlorophenyl | H | 1 | 429 | greenish yellow |

TABLE 11-continued $$Q^1-\underset{\underset{O}{\|}}{C}-\underset{}{\underset{}{\bigcirc}}-N=N-\underset{\underset{HO}{}}{\overset{CH_3}{\underset{}{\bigcirc}}}\overset{SO_3H}{\underset{\underset{Z^o}{|}}{\underset{CH(-CH_2)_a}{\overset{N}{|}}}}-\underset{}{\bigcirc}-SO_3H$$

| Example No. | $Q^1$ | $Z^o$ | a | $\lambda_{max}$ [nm] (in water) | Hue |
|---|---|---|---|---|---|
| 207 | 2,4-dimethylphenyl (CH₃ top, CH₃ bottom-left) | H | 0 | 430 | greenish yellow |
| 208 | 2,4-dimethylphenyl | CH₃ | 1 | 431 | greenish yellow |
| 209 | 2,4-dimethylphenyl | CH₃ | 2 | 431 | greenish yellow |
| 210 | 2,5-dimethylphenyl | H | 0 | 430 | greenish yellow |
| 211 | 2,5-dimethylphenyl | H | 1 | 430 | greenish yellow |
| 212 | 2,3-dimethylphenyl (with CH₃ at 5-position) | CH₃ | 1 | 431 | greenish yellow |
| 213 | 4-isopropyl-3-methylphenyl | H | 1 | 431 | greenish yellow |
| 214 | 4-bromophenyl | H | 1 | 430 | greenish yellow |

TABLE 11-continued

[Structure: Q¹−C(=O)−C₆H₄−N=N− attached to a pyridone ring bearing CH₃, SO₃H, =O, OH, and N−CH(Z°)−(CH₂)ₐ−C₆H₄−SO₃H]

| Example No. | Q¹ | Z° | a | λ_max [nm] (in water) | Hue |
|---|---|---|---|---|---|
| 215 | 2-methyl-4-chlorophenyl (CH₃ ortho, Cl para) | H | 1 | 430 | greenish yellow |
| 216 | 2-methyl-5-chlorophenyl | H | 1 | 429 | greenish yellow |
| 217 | 2-chloro-5-methylphenyl | H | 1 | 430 | greenish yellow |
| 218 | 4-(phenylethyl)phenyl (C₆H₅−CH₂CH₂−C₆H₄−) | H | 1 | 430 | greenish yellow |
| 219 | 4-methoxyphenyl (CH₃O−C₆H₄−) | H | 1 | 432 | yellow |
| 220 | 4-ethoxyphenyl (C₂H₅O−C₆H₄−) | H | 1 | 432 | yellow |
| 221 | 4-methoxy-2-methylphenyl | H | 1 | 432 | yellow |
| 222 | 3,5-dimethylphenyl | H | 1 | 431 | greenish yellow |
| 223 | 3,5-dimethylphenyl | CH₃ | 1 | 431 | greenish yellow |

TABLE 12

Structure: naphthalene with $H_2N$ (top), $Q^2-N=N-$ attached, $HO$, and $SO_3H$ groups.

| Example No. | $Q^2$ | $\lambda_{max}$ [nm] (in water) | Hue |
|---|---|---|---|
| 224 | 2,5-dimethyl-4-sulfo-phenyl — CO — 4-chloro-3-methylphenyl | | bluish red |
| 225 | 2,5-diisopropyl-4-sulfo-phenyl — CO — 3-methylphenyl | | bluish red |
| 226 | 4-$C_7H_{15}(n)$-phenyl — CO — 3-methyl-4-sulfo-phenyl | 513 | bluish red |
| 227 | 4-cyclohexyl-phenyl — CO — 3-methyl-4-sulfo-phenyl | 513 | bluish red |
| 228 | 4-$C_9H_{19}(n)$-phenyl — CO — 3-methyl-4-sulfo-phenyl | 513 | bluish red |
| 229 | 4-$C_{11}H_{23}(n)$-phenyl — CO — 3-methyl-4-sulfo-phenyl | 513 | bluish red |
| 230 | 4-[$C_9H_{19}(n)$-CH(CH$_3$)]-phenyl — CO — 3-methyl-4-sulfo-phenyl | 513 | bluish red |
| 231 | 4-$C_8H_{17}$-3-methyl-phenyl — CO — 3-methyl-4-sulfo-phenyl | 513 | bluish red |

TABLE 13

(structure shown)

| Example No. | $Q^1$ | $Q^3$ | Hue |
|---|---|---|---|
| 232 | 2,4-dimethylphenyl | $CH_2$ | greenish yellow |
| 233 | 2,4-dimethylphenyl | $C_2H_4$ | greenish yellow |
| 234 | 2,5-dimethylphenyl | $CH_2$ | greenish yellow |
| 235 | 2,5-dimethylphenyl | $C_2H_4$ | greenish yellow |

EXAMPLE 236

257 g of 1-(2-phenylethyl)-6-hydroxy-3-cyano-4-methylpyrid-2-one were added at not more than 70° C. to a mixture of 160 g of 100% by weight sulfuric acid and 380 g of 24% by weight oleum. The solution formed was subsequently stirred at 75° C. for 5 hours, producing essentially a product of the formula

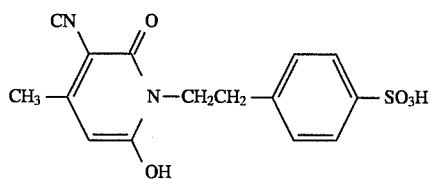

This was followed by heating at 110° C. for 5 hours, during which the cyano group hydrolyzed and the carboxylic acid intermediate was decarboxylated (foaming due to $CO_2$ evolution). Then the reaction mixture was heated to 130°–135° C. and stirred at that temperature for 5.5 hours. After the reaction mixture had cooled down to about 110° C., it was stirred out onto about 900 g of ice-water, and the compound of the formula

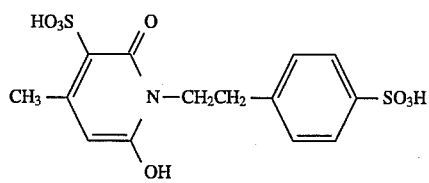

was neutralized at $\leq 30°$ C. with sodium hydroxide solution. This solution can be used directly for preparing azo dyes.

$\lambda_{max}$ ($H_2O$): 325 nm, 247 nm, (minimum at 280 and 235 nm).

We claim:

1. A benzophenoneazo dye of the Formula I

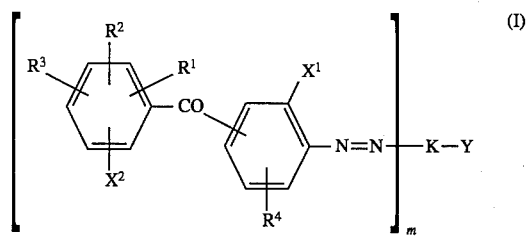

wherein m is 1 or 2;

K is a 6-hydroxypyrid-2-one radical which in ring position 3 is unsubstituted or substituted by carbamoyl, $C_2$–$C_5$-alkanoyl, hydroxysulfonylmethyl or hydroxysulfonyl, the radical of a phenylazopyridone, imidazolopyridine, aminopyrazole, hydroxypyrazole, aminothiazole, pyrimidine, quinolone or aniline coupling component or the radical of a coupling component of the formula IIm

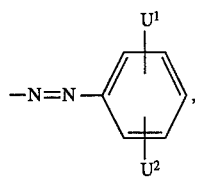

where $Z^{19}$ is amino, phenylamino, $C_{1-4}$-alkanoylamino or benzoylamino, $Z^{20}$ is hydrogen or hydroxyl, and r is 1;

Y, when m is 1, is hydrogen, the radical:

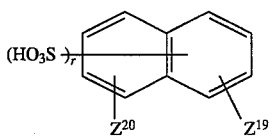

$U^1$ is hydrogen, $C_1$–$C_4$-alkyl or hyroxysulfonyl and $U^2$ is hydrogen, unsubstituted or sulfato-substituted $C_1$–$C_4$-alkyl, hydroxysulfonyl, phenylsulfonyloxy or 6-methyl-7-hydroxysulfonylbenzothiazol-2-yl; or the radical —N=N—$Q^2$, wherein $Q^2$ is the radical of a coupling component, or Y, when m is 2, is hydrogen;

one of the two radicals $X^1$ and $X^2$ is hydrogen and the other is hydroxysulfonyl;

$R^1$, $R^2$ and $R^3$ are identical or different and each is independently of the others hydrogen, halogen, $C_1$–$C_{12}$-alkyl, cyclohexyl, phenyl, 2-hydroxyethylsulfonyl or $C_1$–$C_4$-alkoxy or, when m is 1 and Y is hydrogen, one of $R^1$, $R^2$ or $R^3$ is a radical of the formula:

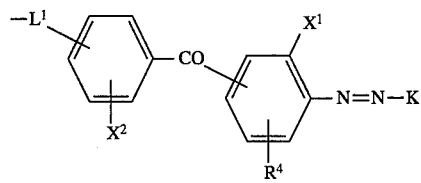

where $L^1$ is a covalent bond, $C_1$–$C_4$-alkylene, oxygen or a radical of the formula O—$CH_2$, O—$CH_2CH_2$—O, O—$CH_2CH_2CH_2$—O or O—$CH(CH_3)CH_2$—O, and $X^1$, $X^2$, $R^4$, and K are each as defined above, and $R^4$ is hydrogen, halogen or $C_1$–$C_4$-alkoxy.

2. A benzophenoneazo dye as claimed in claim 1, wherein $Q^2$ is a radical derived from (i) a compound of formula IIc:

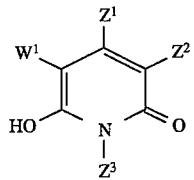

wherein $W^1$ is hydrogen or a radical of the formula

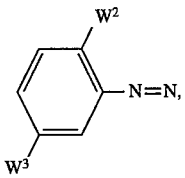

wherein $W^2$ and $W^3$ are identical or different and each is independently of the other hydrogen, methyl, ethyl or methoxy, $Z^1$ is hydrogen, $C_1$–$C_4$-alkyl or phenyl, $Z^2$ is hydrogen, carbamoyl, $C_2$–$C_5$-alkanoyl, hydroxysulfonylmethyl or hydroxysulfonyl, and $Z^3$ is hydrogen or $C_1$–$C_6$-alkyl or $C_1$—$C_3$-alkyl substituted by phenyl or hydroxysulfoylphenyl or $C_1$–$C_3$-alkyl interrupted by from 1 to 3 ether oxygen atoms;

(ii) a compound of formula IId:

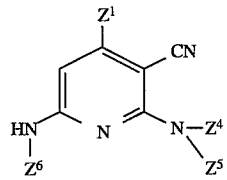

where $Z^4$, $Z^5$ and $Z^6$ are identical or different and each is independently of the others hydrogen, $C_1$–$C_{12}$-alkyl $C_1$–$C_{12}$-alkyl interrupted by from 1 to 4 ether oxygen atoms or $C_1$–$C_{12}$-alkyl substituted by hydroxyl-, phenoxy-, phenyl-, hydroxysulfonylphenyl- or $C_1$–$C_4$-alkanoyloxy, or hydroxysulfonylphenyl or $Z^6$ is 3-(1-imidazolyl)propyl and $Z^5$ is the radical

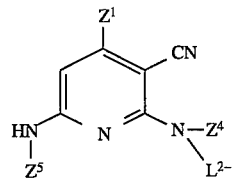

where $L^2$ is $C_2$–$C_4$-alkylene and $Z^1$, $Z^4$ and $Z^5$ are each as defined above, and $Z^1$ is a defined above.

(iii) a compound of formula (IIe):

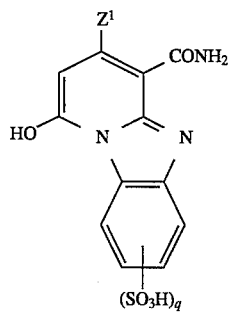

where q is 0 or 1, and $Z^1$ is as defined above;

(iv) a compound of formula (IIf):

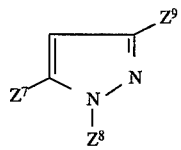

where
- $Z^7$ is amino or hydroxyl.
- $Z^8$ is unsubstituted or phenyl- or hydroxysulfonyl- phenyl-substituted $C_1$–$C_4$-alkyl or substituted or unsubstituted phenyl, and
- $Z^9$ is hydrogen, $C_1$–$C_4$-alkyl, carboxyl or $C_1$–$C_4$-alkoxycarbonyl;

(v) a compound of formula (IIg):

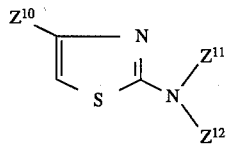

where
- $Z^{10}$ is $C_1$–$C_4$-alkyl, substituted or unsubstituted phenyl or thienyl, and
- $Z^{11}$ and $Z^{12}$ are identical or different and each is independently of the other $C_1$–$C_8$-alkyl or $C_1$–$C_8$-alkyl interrupted by from 1 to 3 ether oxygen atoms;

(vi) a compound of formula (IIh);

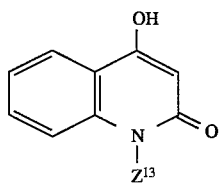

wherein
$Z^{13}$ is $C_1$–$C_4$-alkyl;

(vii) a compound of formula (IIi) or (IIj);

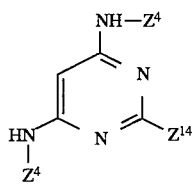

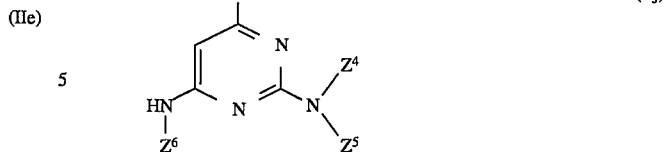

wherein $Z^{14}$ is $C_1$–$C_4$-alkyl or phenyl, and $Z^1$, $Z^4$, $Z^5$ and $Z^6$ are each as defined above;

(viii) a compound of formula (IIk);

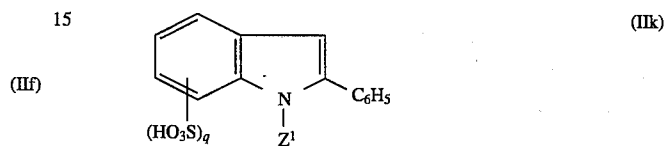

where $Z^1$ and q are each as defined above;

(ix) a compound of formula (II);

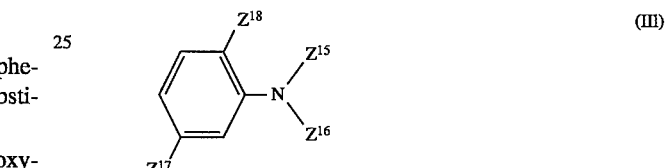

where $Z^{15}$ hydrogen or $C_1$–$C_6$-alkyl unsubstituted or substituted by hydroxyl, $C_1$–$C_4$-alkoxy, cyano, $C_1$–$C_4$-alkanoyloxy, $C_1$–$C_4$-alkoxycarbonyloxy, $C_1$–$C_4$-alkylaminocarbonyloxy, phenyl, hydroxysulfonylphenyl, $C_1$–$C_4$-alkoxycarbonyl or chlorine-, hydroxyl-, $C_1$–$C_4$-alkoxy- or phenoxy-substituted $C_1$–$C_4$-alkoxycarbonyl $Z^{16}$ is hydrogen or $C_1$–$C_6$-alkyl unsubstituted or substituted by phenyl, hydroxysulfonylphenyl, $C_1$–$C_4$-alkoxy carbonyl or chlorine-, hydroxyl-, $C_1$–$C_4$-alkoxy- or phenoxy-substituted $C_1$–$C_4$-alkoxycarbonyl, $Z^{17}$ is hydrogen, $C_1$–$C_4$-alkyl, $C_1$–$C_4$-alkoxy, chlorine, bromine or the radical —NH—CO—Q, where Q is $C_1$–$C_4$-alkyl, $C_1$–$C_4$-alkyl substituted by $C_1$–$C_4$-alkoxy-, phenoxy-, cyano-, hydroxyl-, chlorine- or $C_1$–$C_4$-alkanoyloxy, or unsubstituted or $C_1$–$C_4$-alkoxy-substituted phenoxy, and $Z^{18}$ is hydrogen, $C_1$–$C_4$-alkyl or $C_1$–$C_4$-alkoxy; or

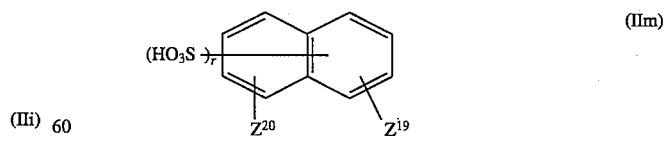

where $Z^{19}$ is amino, phenylamino, $C_1$–$C_4$-alkanoylamino or benzoylamino;

$Z^{20}$ is hydrogen or hydroxyl, and r is 1 or 2.

3. A benzophenoneazo dye as claimed in claim 1 of the formula Ia

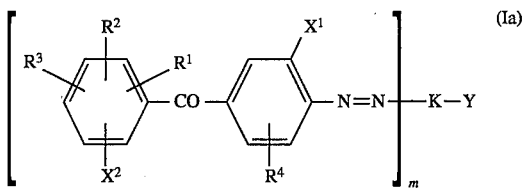

where m, K, Y, $X^1$, $X^2$, $R^1$, $R^2$, $R^3$ and $R^4$ are each as defined above.

4. A benzophenoneazo dye as claimed in claim 1, wherein K is the radical of a pyridone, diaminopyridine, aminopyrazole, pyrimidine, indole or aminonaphthalene coupling component the radical of a coupling component of the formula IIm

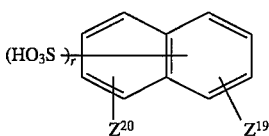

where $Z^{19}$ is amino, phenylamino, $C_1$–$C_4$-alkanoylamino or benzoylamino, $Z^{20}$ is hydrogen or hydroxyl, and r is 1.

5. A benzophenoneazo dye of the formula I

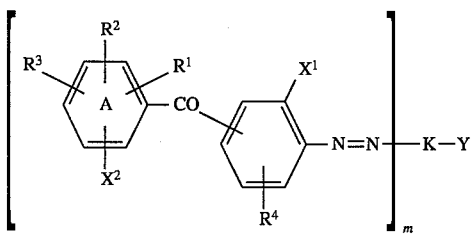

wherein ring A has benzo group fused thereto and optionally has a —$C_2H_4$— group linking ring A to the fused benzo group, m is 1 or 2, K is a 6-hydroxypyrid-2-one radical which in ring position 3 is unsubstituted or substituted by carbamoyl, $C_2$–$C_5$-alkanoyl, hydroxysulfonylmethyl or hydroxysulfonyl, the radical of a phenylazopyridone, imidazolopyridine, aminopyrazole, hydroxypyrazole, aminothiazole, pyrimidine, quinolone or aniline coupling component, or the radical of a coupling component of the formula IIm

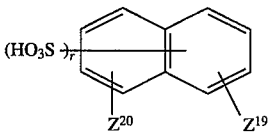

where $Z^{19}$ is amino, phenylamino, $C_1$–$C_4$-alkanoylamino or benzoylamino, $Z^{20}$ is hydrogen or hydroxyl, and r is 1;

Y, when m is 1, is hydrogen, the radical

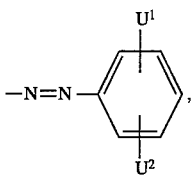

$U^1$ is hydrogen, $C_1$–$C_4$-alkyl or hydroxysulfonyl and $U^2$ is hydrogen, unsubstituted or sulfato-substituted $C_1$–$C_4$-alkyl, hydroxysulfonyl, phenylsulfonyloxy or 6-methyl-7-hydroxysulfonylbenzothiazol-2-yl;

or the radical —N=N—$Q^2$, wherein $Q^2$ is the radical of coupling component, or, Y, when m is 2, is hydrogen, one of the two radicals $X^1$ and $X^2$ is hydrogen and the other is hydroxysulfonyl;

$R^1$, $R^2$ and $R^3$ are identical or different and each is independently of the others hydrogen, halogen, $C_1$–$C_{12}$-alkyl, cyclohexyl, phenyl, 2-hydroxyethylsulfonyl or $C_1$–$C_4$-alkoxy or, when m is 1 and Y is hydrogen, one of $R^1$, $R^2$ or $R^3$ is a radical of the formula:

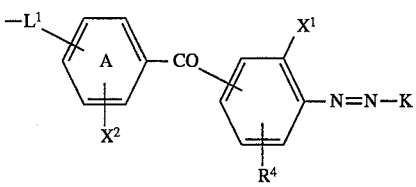

where $L^1$ is a covalent bond, $C_1$–$C_4$-alkylene, oxygen or a radical of the formula O—$CH_2$, O—$CH_2CH_2$—O, O—$CH_2CH_2CH_2$—O or O—CH($CH_3$)$CH_2$—O, and $X^1$, $X^2$, $R^4$, K and the ring A are each as defined above, and $R^4$ is hydrogen, halogen or $C_1$–$C_4$-alkoxy.

6. A benzophenoneazo dye as claimed in claim 5, wherein $Q^2$ is a radical derived from (i) a compound of formula IIc:

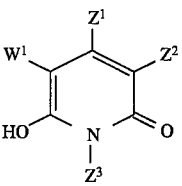

wherein $W^1$ is hydrogen or a radical of the formula

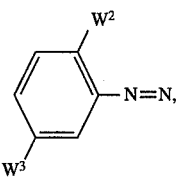

wherein $W^2$ and $W^3$ are identical or different and each is independently of the other hydrogen, methyl, ethyl or methoxy, $Z^1$ is hydrogen, $C_1$–$C_4$-alkyl or phenyl, $Z^2$ is hydrogen, carbamoyl, $C_2$–$C_5$-alkanoyl, hydroxysulfonylmethyl or hydroxysulfonyl, and $Z^3$ is hydrogen or $C_1$–$C_3$-alkyl or $C_1$–$C_3$-alkyl substituted by phenyl or hydroxysulfonylphenyl or $C_1$–$C_3$-alkyl interrupted by from 1 to 3 ether oxygen atoms;

(ii) a compound of formula IId:

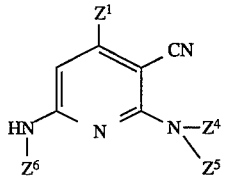

(IId)

where $Z^4$, $Z^5$ and $Z^6$ are identical or different and each is independently of the others hydrogen, $C_1$–$C_{12}$-alkyl $C_1$–$C_{12}$-alkyl interrupted by from 1 to 4 ether oxygen atoms or $C_1$–$C_{12}$-alkyl substituted by hydroxyl-, phenoxy-, phenyl-, hydroxysulfonylphenyl- or $C_1$–$C_4$-alkanoyloxy, or hydroxysulfonylphenyl or $Z^6$ is 3-(1-imidazolyl)propyl and $Z^5$ is the radical

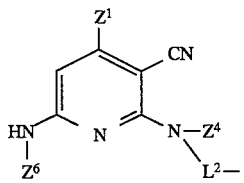

where $L^2$ is $C_2$–$C_4$-alkylene and $Z^1$, $Z^4$ and $Z^5$ are each as defined above, and $Z^1$ is as defined above.

(iii) a compound of formula (IIe):

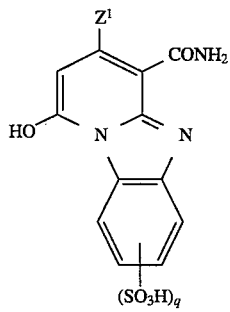

(IIe)

where q is 0 or 1, and $Z^1$ as defined above;

(iv) a compound of formula (IIf):

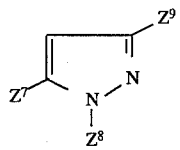

(IIf)

where $Z^7$ is amino or hydroxyl.

$Z^8$ is unsubstituted or phenyl- or hydroxysulfonyl-phenyl-substituted $C_1$–$C_4$-alkyl or substituted or unsubstituted phenyl, and $Z^9$ is hydrogen, $C_1$–$C_4$-alkyl, carboxyl or $C_1$–$C_4$-alkoxycarbonyl;

(v) a compound of formula (IIg):

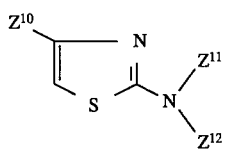

(IIg)

where $Z^{10}$ is $C_1$–$C_4$-alkyl, substituted or unsubstituted phenyl or thienyl, and $Z^{11}$ and $Z^{12}$ are identical or different and each is independently of the other $C_1$–$C_8$-alkyl or $C_1$–$C_8$-alkyl interrupted by from 1 to 3 ether oxygen atoms;

(vi) a compound of formula (IIh);

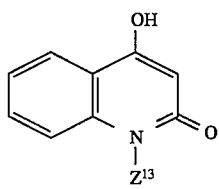

(IIh)

wherein $Z^{13}$ is $C_1$–$C_4$-alkyl;

(vii) a compound of formula (IIi) or (IIj);

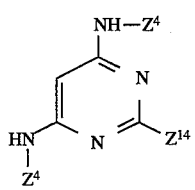

(IIi)

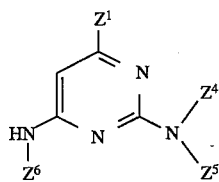

(IIj)

wherein $Z^{14}$ is $C_1$–$C_4$-alkyl or phenyl, and $Z^1$, $Z^4$, $Z^5$ and $Z^6$ are each as defined above;

(viii) a compound of formula (IIk);

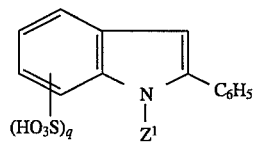

(IIk)

where $Z^1$ and q are each as defined above;

(ix) a compound of formula (III);

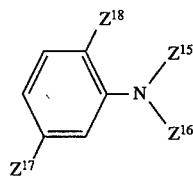

(III)

where $Z^{15}$ is hydrogen $C_1$–$C_6$-alkyl unsubstituted or substituted by hydroxyl, $C_1$–$C_4$-alkoxy, cyano, $C_1$–$C_4$-alkanoyloxy, $C_1$–$C_4$-alkoxycarbonyloxy, $C_1$–$C_4$-alkylaminocarbonyloxy, phenyl, hydroxysulfonylphenyl, $C_1$–$C_4$-alkoxycarbonyl of chlorine-, hydroxyl-, $C_1$–$C_4$-alkoxy- or phenoxy-substituted $C_1$–$C_4$-alkoxycarbonyl $Z^{16}$ is hydrogen or $C_1$–$C_6$-alkyl or $C_1$–$C_6$-alkyl substituted by phenyl, hydroxysulfonylphenyl, $C_1$–$C_4$-alkoxycarbonyl or chlorine-, hydroxyl-, $C_1$–$C_4$-alkoxy- or phenoxy-substituted $C_1$–$C_4$-alkoxycarbonyl, $Z^{17}$ is hydrogen, $C_1$–$C_4$-alkyl, $C_1$–$C_4$-alkoxy, chlorine, bromine or the radical —NH—CO—Q, where Q is $C_1$–$C_4$-alkyl, unsubstituted or substituted by $C_1$–$C_4$-alkoxy-, phenoxy-, cyano-, hydroxyl-, chlorine- or $C_1$–$C_4$-alkanoyloxy, or unsubstituted or $C_1$–$C_4$-alkoxy-substituted phenoxy, and $Z^{18}$ is hydrogen, $C_1$–$C_4$-alkyl or $C_1$–$C_4$-alkoxy; or

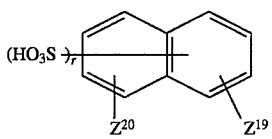

(IIm)

where $Z^{19}$ is amino, phenylamino, $C_1$–$C_4$-alkanoylamino or benzoylamino, $Z^{20}$ is hydrogen or hydroxyl, and r is 1 or 2.

7. A benzophenoneazo dye as claimed in claim 5 of the formula Ia

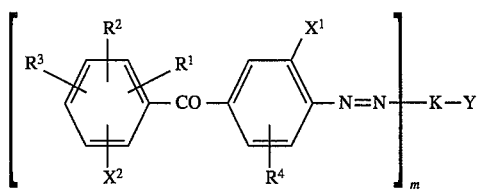

(Ia)

where m, K, Y, $X^1$, $X^2$, $R^1$, $R^2$, $R^3$ and $R^4$ are each as defined above.

8. A benzophenoneazo dye as claimed in claim 5, wherein K is the radical of a pyridone, diaminopyridine, aminopyrazole, pyrimidine, indole or aminonaphthalene coupling component or the radical of a coupling component of the formula IIm

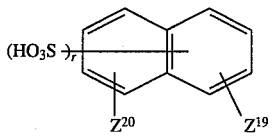

(IIm)

where $Z^{19}$ is amino, phenylamino, $C_1$–$C_4$-alkanoylamino or benzoylamino, $Z^{20}$ is hydrogen or hydroxyl, and r is 1.

9. A benzophenoneazo dye as claimed in claim 1, wherein K is a radical of a coupling component of formula (IIm).

10. A benzophenoneazo dye as claimed in claim 1, wherein $Q^2$ is a radical of a compound of formula (IIc).

11. A benzophenoneazo dye as claimed in claim 1, wherein $Q^2$ is a radical of a compound of formula (IId).

12. A benzophenoneazo dye as claimed in claim 1, wherein $Q^2$ is a radical of a compound of formula (IIi).

13. A benzophenoneazo dye as claimed in claim 1, wherein $R^4$ is halogen or $C_1$–$C_4$-alkoxy.

14. A benzophenoneazo dye as claimed in claim 5, wherein K is a radical of a coupling component of formula (IIm).

15. A benzophenoneazo dye as claimed in claim 5, wherein $Q^2$ is a radical of a compound of formula (IIc).

16. A benzophenoneazo dye as claimed in claim 5, wherein $Q^2$ is a radical of a compound of formula (IId).

17. A benzophenoneazo dye as claimed in claim 5, wherein $Q^2$ is a radical of a compound of formula (IIi).

18. A benzophenoneazo dye as claimed in claim 5, wherein $R^4$ is halogen or $C_1$–$C_4$-alkoxy.

19. A benzophenoneazo dye as claimed in claim 1, wherein $X^1$ is hydroxysulfonyl.

20. A benzophenoneazo dye as claimed in claim 5, wherein $X^1$ is hydroxysulfonyl.

21. A benzophenoneazo dye as claimed in claim 1, wherein $X^2$ is hydroxysulfonyl.

22. A benzophenoneazo dye as claimed in claim 5, wherein $X^2$ is hydroxysulfonyl.

23. A method of dyeing natural or synthetic substrates, comprising: dyeing said natural or synthetic substrates with the benzophenone azo dye of claim 1.

24. A method of dyeing natural or synthetic substrates, comprising: dyeing said natural or synthetic substrates with the benzophenone azo dye of claim 5.

* * * * *

UNITED STATES PATENT AND TRADEMARK OFFICE
CERTIFICATE OF CORRECTION

PATENT NO. :  5,510,468
DATED      :  April 23, 1996
INVENTOR(S) :  Gunther LAMM, et al.

It is certified that error appears in the above-indentified patent and that said Letters Patent is hereby corrected as shown below:

On the title page, Item [62], the Related U.S. Application Data, should read:

--Division of Ser. No. 87,792, filed PCT/EP92/00281, Feb. 10, 1992, Pat. No. 5,380,859--

Signed and Sealed this

Sixth Day of August, 1996

*Attest:*

BRUCE LEHMAN

*Attesting Officer*   *Commissioner of Patents and Trademarks*